United States Patent [19]

Schwarz et al.

[11] 4,446,147
[45] May 1, 1984

[54] AZAPROSTACYCLINS, THEIR PREPARATION AND PHARMACEUTICAL USE

[75] Inventors: Norbert Schwarz; Werner Skuballa; Helmut Vorbrueggen; Jorge Casals-Stenzel; Ekkehard Schillinger; Michael H. Town, all of Berlin, Fed. Rep. of Germany

[73] Assignee: Schering Aktiengesellschaft, Berlin and Bergkamen, Fed. Rep. of Germany

[21] Appl. No.: 350,674

[22] Filed: Feb. 22, 1982

[30] Foreign Application Priority Data

Feb. 20, 1981 [DE] Fed. Rep. of Germany ....... 3107100

[51] Int. Cl.³ .................. C07D 209/52; A61K 31/40
[52] U.S. Cl. .................................. 424/274; 546/272; 548/452; 548/467
[58] Field of Search ............... 548/452, 467; 424/274; 546/272

[56] References Cited

U.S. PATENT DOCUMENTS

| 4,097,489 | 6/1978 | Bundy | 560/121 |
|---|---|---|---|
| 4,211,706 | 7/1980 | Bundy | 548/452 |
| 4,315,013 | 2/1982 | Skuballa | 548/452 |

OTHER PUBLICATIONS

G. L. Bundy et al., Tetrahedron Letters No. 16, pp. 1371-1374, 1978, Pergamon Press.

*Primary Examiner*—Robert Gerstl
*Attorney, Agent, or Firm*—Millen & White

[57] ABSTRACT

Azaprostacyclins of Formula I

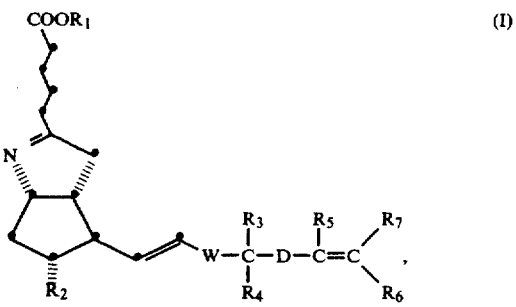

wherein
$R_1$ is hydrogen, alkyl, cycloalkyl, aryl, a heterocyclic residue, or a phenacyl residue optionally substituted on the phenyl ring by bromine, phenyl, alkoxy, or dialkoxy,
W is a free or functionally modified carbonyl group or a

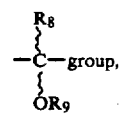

wherein $R_8$ is hydrogen or alkyl of 1–5 carbon atoms and $R_9$ is hydrogen or a readily cleavable ether or acyl residue and wherein the $OR_9$-group can be in the α- or β-position,
$R_2$ is a free or functionally modified hydroxy group.

20 Claims, No Drawings

AZAPROSTACYCLINS, THEIR PREPARATION AND PHARMACEUTICAL USE

BACKGROUND OF THE INVENTION

The present invention relates to novel prostacyclin derivatives, a process for their production, and their use as medicinal agents.

Prostacyclin ($PGI_2$), one of the primary factors in blood platelet aggregation, has a dilating effect on various blood vessels (Science 196: 1072) and therefore is considered as an agent for lowering blood pressure. $PGI_2$ does not, however, possess the stability required for a medicinal agent. For example, the half-life of $PGI_2$ at physiological pH values and at room temperature is only a few minutes.

9α,6-Nitriloprostaglandins have been reported in a publication of Upjohn (Bundy et al, Tetrahedron Letters 1978: 1371) as well as in DOS [German Unexamined Laid-Open Application] No. 2,826,096. These references are incorporated by reference herein.

SUMMARY OF THE INVENTION

It is an object of this invention to provide improved prostaglandin-type compounds.

Upon further study of the specification and appended claims, further objects and advantages of this invention will become apparent to those skilled in the art.

These objects have been attained by providing azaprostacyclins of Formula I

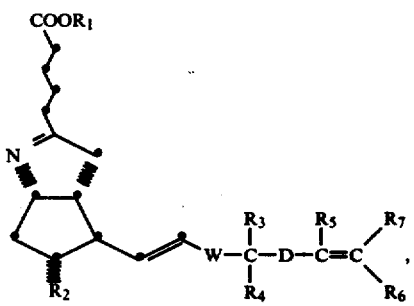

wherein $R_1$ is hydrogen, alkyl, cycloalkyl, aryl, a heterocyclic residue, or a phenacyl residue optionally substituted on the phenyl ring by bromine, phenyl, alkoxy, or dialkoxy, W is free or functionally modified carbonyl or a

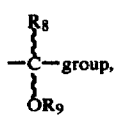

wherein $R_8$ is hydrogen or alkyl of 1-5 carbon atoms and $R_9$ is hydrogen or a readily cleavable ether or acyl residue and wherein the $OR_9$-group is in the α- or β-position, $R_2$ is a free or functionally modified hydroxy group, $R_3$ and $R_4$ each independently is hydrogen, alkyl of 1-5 carbon atoms, or fluorine, D is alkylene of 1-2 carbon atoms optionally substituted by alkyl of 1-5 carbon atoms, $R_5$ is hydrogen or alkyl of 1-2 carbon atoms or, when D is alkylene of 1 or 2 carbon atoms, optionally substituted, represents a bond with $R_6$, $R_6$ and $R_7$ each is hydrogen or alkyl of 1-2 carbon atoms wherein $R_6(R_7)$ is halogen if $R_7(R_6)$ is alkyl of 1-2 carbon atoms, or $R_5$ and $R_7$ each independently is hydrogen or alkyl of 1-2 carbon atoms, and D and $R_6$ form a ring closed via $(CH_2)_{1-3}$ with D as

and $R_6$ as $-CH_2-$, and, when $R_1$ is hydrogen, physiologically compatible salts thereof with bases.

That is, the following are possible embodiments of the structural features represented by D, $R_5$, $R_6$ and $R_7$.

D can be $-(CH_2)_{1-2}-$, optionally substituted by 1-2 $C_{1-5}$-alkyl groups, or, together with $R_6$ can form a closed carbocyclic ring, i.e., $-D-$ can be

and $R_6$ is $-CH_2-$ joined to $-D-$ by $-(CH_2)_{1-3}-$ to form the group

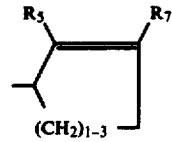

i.e. to form unsaturated cycloalkyl groups of 5, 6, or 7 carbon atoms.

When D is optionally substituted alkylene, $R_5$ can be H, $C_{1-2}$-alkyl or, together with $R_6$, can form a bond; when $R_5$ is H or $C_{1-2}$-alkyl, $R_6/R_7$ can be H/H, $C_{1-2}$-alkyl/$C_{1-2}$-alkyl, H/$C_{1-2}$-alkyl or vice versa, or $C_{1-2}$-alkyl/halo or vice versa; and when $R_5/R_6$ is a bond, $R_7$ can be H or $C_{1-2}$-alkyl.

When D, together with $R_6$, forms a ring, $R_5$ can be H or $C_{1-2}$ alkyl and $R_7$ can be H or $C_{1-2}$-alkyl.

Thus, the compounds of this invention include those of the formula

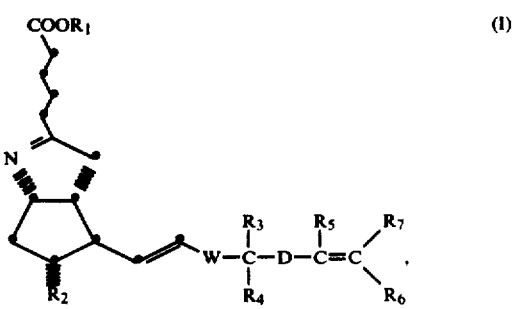

wherein $R_1$ is (a) hydrogen, (b) $C_{1-10}$ alkyl, (c) $C_{1-10}$ alkyl substituted by halogen; $C_{1-4}$ alkoxy; $C_{6-10}$ aryl; $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group; di-$C_{1-4}$ alkylamino; or tri-$C_{1-4}$-alkylammonium; (d) $C_{4-10}$ cycloalkyl, (e) $C_{4-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, (h) an aromatic heterocycle of 5 or 6 ring atoms one of which is O, N or S, the remainder being carbon atoms, (i) phenacyl, or (j) phenacyl substituted on the phenyl ring by bromine, phenyl, $C_{1-4}$-alkoxy, or di-$C_{1-4}$-alkoxy,

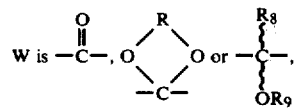

wherein $R_8$ is hydrogen or alkyl of 1-5 carbon atoms, $R_9$ is hydrogen, tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid, the $OR_9$-group can be in the α- or β-position, and R is —$(CH_2)_{2-5}$—,

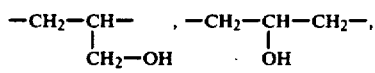

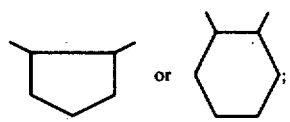

$R_2$ is OH or $OR_9$, $R_3$ and $R_4$ each independently is hydrogen, alkyl of 1-5 carbon atoms, or fluorine, D is —$(CH_2)_{1\ or\ 2}$—, —$(CH_2)_{1\ or\ 2}$— substituted by $C_{1-5}$-alkyl or together with $R_6$ forms a ring of the formula

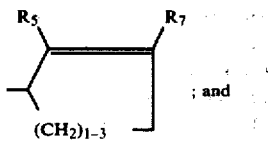

(1) when D is optionally substituted alkylene as defined above, $R_5$ is H, $C_{1-2}$-alkyl or together with $R_6$ forms a bond; when $R_5$ is H or $C_{1-2}$-alkyl, $R_6$ and $R_7$ each independently is H or $C_{1-2}$-alkyl or one is $C_{1-2}$alkyl and the other is halo; when $R_5/R_6$ is a bond, $R_7$ is H or $C_{1-2}$-alkyl; and (2) when D forms a ring with $R_6$, $R_5$ and $R_7$ each independently is H or $C_{1-2}$alkyl; or for the compounds wherein $R_1$ is H, the physiologically compatible salt thereof.

DETAILED DISCUSSION

It has now been found that a prolonged duration of activity, higher selectivity, and improved efficacy can be achieved by the introduction of double and triple bonds and, optionally, alkyl groups, into the lower chain of 9-desoxy-9α,6-nitrilo-PGF.

The alkyl group $R_1$ can be straight chained or branched alkyl of 1-10 carbon atoms, e.g. methyl, ethyl, propyl, butyl, isobutyl, tert-butyl, pentyl, neopentyl, heptyl, hexyl, decyl and the like. The alkyl groups $R_1$ can optionally be mono- to poly-substituted (e.g., 1-2 substituents) by halogen (e.g., F, Cl, Br) atoms, $C_{1-4}$-alkoxy, optionally substituted $C_{6-10}$ aryl, di-$C_{1-4}$-alkylamino, and tri-$C_{1-4}$-alkylammonium. Mono-substituted alkyl groups are preferred when alkyl is substituted. Suitable substituted aryl group substituents include those substituted aryl groups disclosed below for $R_1$ groups per se.

Examples of suitable sutstituents include fluorine, chlorine, or bromine atoms, phenyl, dimethylamino, diethylamino, methoxy, ethoxy, etc. Preferred alkyl groups $R_1$ are those of 1-4 carbon atoms, such as, for example, methyl, ethyl, propyl, dimethylaminopropyl, isobutyl, and butyl.

Suitable aryl groups $R_1$ are substituted as well as unsubstituted aryl groups, of 6-10 carbon atoms e.g. phenyl, 1-naphthyl, and 2-naphthyl, each of which can optionally be substituted by 1-3 halogen atoms, a phenyl group, 1-3 alkyl groups of 1-4 carbon atoms each; or a chloromethyl, fluoromethyl, trifluoromethyl, carboxy, hydroxy, or alkoxy group of 1-4 carbon atoms. Substitution in the 3- and 4-positions of the phenyl ring is preferred, for example substitution by fluorine, chlorine, alkoxy, or trifluoromethyl, or, in the 4-position, by hydroxy.

The cycloalkyl group $R_1$ can contain 4-10 ring atoms, preferably 5 or 6 carbon atoms. The rings can optionally be substituted by alkyl groups of 1-4 carbon atoms. Examples include cyclopentyl, cyclohexyl, methylcyclohexyl, and adamantyl.

Suitable heterocyclic groups $R_1$ are 5- and 6-membered heterocycles, generally aromatic, containing at least one and preferably one hetero atom, preferably nitrogen, oxygen, or sulfur, the remainder being C-atoms. Examples include 2-furyl, 2-thienyl, 2-pyridyl, 3-pyridyl, 4-pyridyl, 3-thienyl, etc.

Suitable substituents on the phenyl ring of the phenacyl groups include $C_{1-4}$-alkoxy and di-$C_{1-4}$-alkoxy, generally in the 3 and 4 positions.

The hydroxy groups $R_2$ and those in W can be functionally modified, for example by etherification or esterification, wherein the free or modified hydroxy groups in W can be in the α- or β-position, free hydroxy groups being preferred. Suitable ether and acyl residues are fully conventional residues known to persons skilled in the art. Ether residues which can be readily split off are preferred, such as, for example, tetrahydropyranyl, tetrahydrofuranyl, α-ethoxyethyl, trimethylsilyl, dimethyl-tert-butylsilyl, and tribenzylsilyl residues. Acyl residues include those of $C_{1-15}$-hydrocarbon carboxylic or sulfonic acids, for example: acetyl, propionyl, butyryl, benzoyl, etc.

Functionally modified carbonyl groups are understood to include ketal groups, e.g. —O—$(CH_2)_{2-5}$—O—,

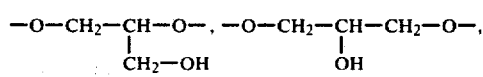

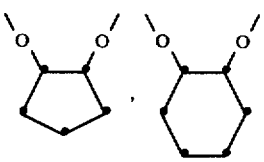

Suitable alkyl groups $R_3, R_4, R_8$ and suitable substituents for the alkylene group D include straight-chain and branched alkyl residues of 1-5 carbon atoms, e.g. methyl, ethyl, propyl, isopropyl, butyl, isobutyl, tert-butyl, pentyl, isopentyl and neopentyl. Methyl and ethyl are preferred.

Suitable halogens $R_6$ or $R_7$ include fluorine, chlorine, bromine, and iodine. Fluorine and chlorine are preferred.

For salt formation with the free acids ($R_1 = H$), conventional inorganic and organic bases can be employed. These are known to persons skilled in the art for the formation of physiologically compatible salts. Typical examples include alkali metal hydroxides, such as sodium and potassium hydroxide, alkaline earth metal hydroxides, such as calcium hydroxide, ammonia, amines, such as ethanolamine, diethanolamine, triethanolamine, N-methylglucamine, morpholine, tris(hydroxymethyl) methylamine, amino acids, such as arginine, etc.

The present invention furthermore relates to a process for the preparation of the azaprostacyclins of this invention comprising in fully conventional manner, subjecting a compound of Formula II

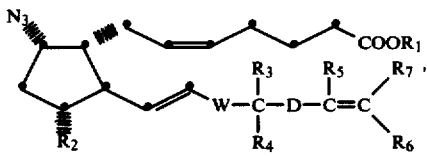

wherein $R_1$, $R_2$, $R_3$, $R_4$, $R_5$, $R_6$, $R_7$, W, and D are as defined above, to a thermal treatment in an inert solvent and optionally, subsequently, and conventionally, in any desired sequence, liberating blocked hydroxy groups and/or esterifying or etherifying free hydroxy groups and/or esterifying free carboxy groups and/or saponifying an esterified carboxy group, or converting a carboxy group into a physiologically compatible salt with a base.

The thermal reaction of the compound of Formula II is carried out at temperatures of 20°-150° C., preferably 40°-120° C. for a time period of generally, 5-36 hours. Examples of suitable inert solvents, especially for the preferred temperature range, include: ethyl acetate, methyl acetate, tetrahydrofuran, dimethoxyethane, carbon tetrachloride, methylene chloride, 1,2-dichloroethane, dimethylformamide, etc.

Saponification of the prostaglandin esters can be conducted according to methods known to those skilled in the art, for example, with alkaline catalysts. The introduction of an ester group wherein $R_1$ is an alkyl group of 1-10 carbon atoms also can be achieved according to methods known to persons skilled in the art. The carboxy compounds are reacted, for example, with diazo hydrocarbons in a conventional fashion. The esterification with diazo hydrocarbons takes place, for example, by mixing a solution of the diazo hydrocarbon in an inert solvent, preferably in diethyl ether, with the carboxy compound in the same or in another inert solvent, such as, for example, methylene chloride. After the reaction is completed within 1-30 minutes, the solvent is removed and the ester purified as usual. Diazoalkanes are either known or can be produced by following conventional methods [Org. Reactions 8: 389-394 (1954)].

The ester group $R_1$ wherein $R_1$ is a substituted or unsubstituted aryl group is introduced according to methods known to persons skilled in the art. For example, the carboxy compounds can be reacted with the corresponding arylhydroxy compounds with dicyclohexylcarbodiimide in the presence of a suitable base, e.g. pyridine or triethylamine, in an inert solvent. Suitable solvents include methylene chloride, ethylene chloride, chloroform, ethyl acetate, tetrahydrofuran, preferably chloroform. The reaction is generally conducted at temperatures of −30° to +50° C., preferably at +10° C.

The esters wherein $R_1$ is optionally substituted phenacyl can be prepared fully analogously to Weygand-Hilgetag, J. A. Barth, Leipzig, 1970, page 197.

The prostacyclin derivatives of Formula I wherein $R_1$ is a hydrogen atom can be converted into salts with suitable quantities of the corresponding inorganic bases under normal neutralization conditions. For example, when dissolving the corresponding PG acids in water containing the stoichiometric amount of the base, the solid inorganic salt is obtained after evaporation of the water or after the addition of a water-miscible solvent, e.g. alcohol or acetone.

To produce an amine salt, which is done in the usual way, the PG acid is dissolved, for example, in a suitable solvent such as ethanol, acetone, diethyl ether, or benzene, and at least the stoichiometric quantity of the amine is added to this solution. During this step, the salt is ordinarily obtained in the solid form or is isolated as usual after evaporation of the solvent.

The functional modification of the free OH-groups can be effected also according to methods known to persons skilled in the art. To introduce the ether blocking groups, for example, the reaction is conducted with dihydropyran in methylene chloride or chloroform with the use of an acidic condensation agent, e.g. p-toluene-sulfonic acid. The dihydropyran is employed in excess, preferably in amounts twice to ten times the theoretical requirement. The reaction is normally completed at 0°-30° C. after 15-30 minutes. The acyl blocking groups are introduced by conventionally reacting a compound of Formula I with a carboxylic acid derivative, e.g. an acid chloride, acid anhydride, etc.

The liberation of a functionally modified OH-group to obtain other compounds of Formula I also takes place according to methods known per se. For example, ether blocking groups can be split off in an aqueous solution of an organic acid, e.g. acetic acid, propionic acid, etc. To improve solubility, a water-miscible, inert organic solvent is suitably added. Suitable organic solvents include, for example, alcohols, such as methanol and ethanol, and ethers, such as dimethoxyethane, dioxane, and tetrahydrofuran. Tetrahydrofuran is preferably employed. The splitting-off step is carried out preferably at temperatures of 20° to 80° C.

The silyl ether blocking groups are split off, for example, with tetrabutylammonium fluoride. Examples of suitable solvents include tetrahydrofuran, diethyl ether, dioxane, methylene chloride, etc. The splitting-off step is preferably conducted at temperatures of 0° to 80° C.

The acyl groups can be saponified, for example, with alkali or alkaline earth metal carbonates or hydroxides in an alcohol or in the aqueous solution of an alcohol. Suitable alcohols include aliphatic alcohols, such as, for example, methanol, ethanol, butanol, etc., preferably methanol. Suitable alkali metal carbonates and hydroxides are potassium and sodium salts, but the potassium salts are preferred. Examples of suitable alkaline earth metal carbonates and hydroxides are calcium carbonate, calcium hydroxide, and barium carbonate. The reaction takes place at −10° to 70° C., preferably at 25° C.

The azide of Formula II utilized as the starting material for the aforedescribed process can be conventionally prepared by converting the corresponding partially known alcohols of Formula III

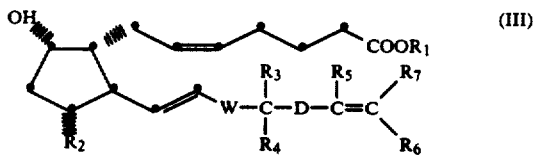

(at least partially disclosed in or preparable by methods disclosed in DOS No. 2,729,960 and its equivalent U.S. Pat. No. 4,235,930 whose disclosures are incorporated by reference herein (see also below)), wherein free hydroxy groups in $R_2$ and W are blocked, for example, as tetrahydropyranyl ethers, with p-toluenesulfonic acid chloride into the tosylate of Formula IV

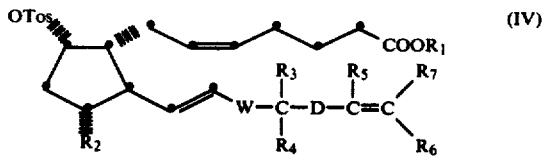

In these formulae, all symbols are as defined above.

By conventional reaction with potassium nitrite in dimethyl sulfoxide, the 9β-configured alcohol V is obtained

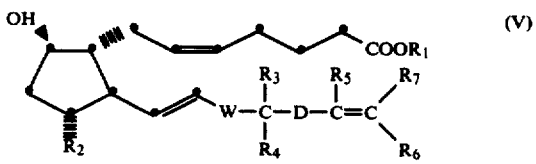

which is reacted with p-toluenesulfonic acid chloride in the presence of pyridine to the tosylate of Formula VI

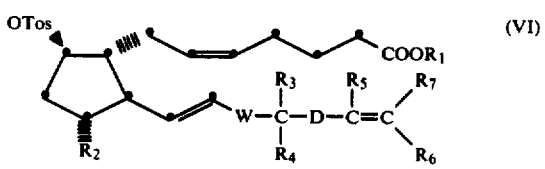

At this stage, the tetrahydropyranyl ether blocking group can be split off, if desired. The tosylate is thereafter conventionally converted with sodium azide in a polar, aprotic solvent, such as DMF, N-methylpyrrolidone, or preferably HMPA (hexamethylphosphoric triamide), into the azide of Formula II which is thereafter optionally saponified ($R_1$=H).

The foregoing reactions are conventional and in conjunction with the following disclosure regarding preparation of intermediates of Formula III and the following examples, all compounds of this invention can readily be prepared. The reactions for preparing the starting materials of Formula II are further exemplified below and are fully conventional (see e.g. U.S. patent application Ser. No. 122,794 of Feb. 19, 1980 corresponding to German Pat. No. 29 07 118).

The compounds of this invention have blood-pressure-lowering and bronchodilatory effects. They are furthermore suitable for inhibition of thrombocyte aggregation.

The novel prostacyclin derivatives of this invention thus constitute valuable pharmaceutically active agents for administration to mammals, including humans. Moreover, with a similar spectrum of effectiveness, they exhibit, as compared with corresponding prostaglandins, a higher specificity and, above all, a substantially longer efficacy. As compared with $PGI_2$, they are distinguished by a higher stability. The high tissue specificity of the novel prostaglandins can be demonstrated in a study on smooth-muscle organs, such as, for example, on the guinea pig ileum or on the isolated rabbit trachea, where a substantially lower stimulation can be observed than in the administration of natural prostaglandins of the E, A, or F type. As contrasted to comparable prostacyclins, several of these novel azaprostacyclins are distinguished by a strong dissociation of efficacy, i.e., enhanced selectivity. They lower the blood pressure with only a minor inhibition of thrombocyte aggregation.

The novel prostacyclin analogs possess the properties typical for prostacyclins, such as, for example, lowering of peripheral arterial and coronary vascular resistance, myocardial cytoprotection and thus lowering of systemic blood pressure without lowering at the same time the stroke volume and coronary blood flow; treatment of stroke, prophylaxis and therapy of coronary heart disease, coronary thrombosis, cardiac infarction, peripheral arterial diseases, arteriosclerosis, and thrombosis; prophylaxis and therapy of ischaemic attacks of the CNS-system; therapy for shock; inhibition of bronchoconstriction, inhibition of gastric acid secretion, and cytoprotection of gastric and intestinal mucosa, cytoprotection in the live and pancreas; antiallergic properties; lowering of the pulmonary vascular resistance and pulmonary blood pressure, stimulation of kidney blood suffusion; usage in place of heparin or as adjuvant in the dialysis of hemofiltration; inhibition of labor, treatment of gestational toxicosis [gestosis]; increase of cerebral blood flow, etc. Furthermore, the novel prostaglandin analogs have antiproliferative properties. The prostacyclines of the invention can also be used in combination, for example with β-blockers or diuretics.

The dosage of the compounds is generally 1–1,500 μg/kg/day, when administered to human patients. The typical unit dosage for the pharmaceutically acceptable vehicle is 0.01–100 mg.

For example, when injecting the compounds of this invention in doses of 5, 20, and 100 μg/kg of body weight intravenously into nonanesthetized, hypertonic rats, they show a stronger blood-pressure-lowering activity of a longer duration than $PGE_2$ and $PGA_2$, without triggering diarrhea, as does $PGE_2$, or cardiac arrythmias, as does PGA$_2$. Upon intravenous injection into anesthetized rabbits, the compounds of this invention show, as compared with PGE$_2$ and PGA$_2$, a stronger and considerably more prolonged blood-pressure-lowering effect without affecting other smooth-muscle organs or organ functions.

The novel prostaglandin analogs of this invention are substantially more selective with regard to potency, as compared with known PG analogs in causing prostaglandin-like biological responses, and have a substantially longer duration of biological activity. Accordingly, each of these novel prostaglandin analogs is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

The galenic pharmacy is fully analogous to that of other PG compounds. For example, sterile, injectable aqueous or oily solutions can be used for parenteral administration. Suitable for oral administration are, for example, tablets, dragees, or capsules. Accordingly, this invention also relates to medicvnal agents based on the compounds of this invention and customary adjuvants and vehicles. The active agents of this invention then can be used in conjunction with the adjuvants known and customary in galenic pharmacy, for example for the preparation of blood-pressure-lowering drugs.

The present invention further relates to novel intermediates of Formula IIIa

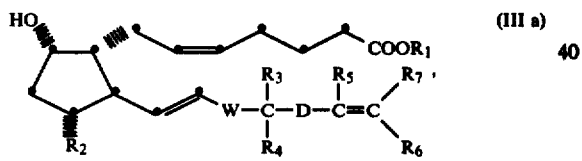
(III a)

wherein

R$_1$, W, R$_2$, R$_3$, and R$_4$ are as defined for Formula I,

D is alkylene of 1-2 carbon atoms optionally substituted by alkyl groups of 1-5 carbon atoms, R$_5$ together with R$_6$ is an additional bond, if D is an optionally with C$_{1-5}$-alkyl substituted ethylene group, and R$_7$ is hydrogen or C$_{1-2}$-alkyl or R$_5$ and R$_7$ are independently each hydrogen or alkyl of 1-2 carbon atoms and D and R$_6$ form a ring closed via (CH$_2$)$_{1-3}$ with D as

and R$_6$ as —CH$_2$—.

R$_7$ is hydrogen or C$_{1-2}$-alkyl or

R$_5$ and R$_7$ are independently each hydrogen or alkyl of 1-2 carbon atoms and D and R$_6$ form a ring closed via (CH$_2$)$_{1-3}$.

The latter grouping

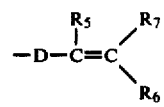

accordingly has the following structure:

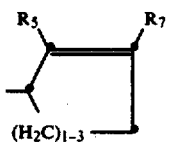

Typical examples of the novel compounds of Formula IIIa include:

(5Z,13E)-(8R,9S,11R,12R,15S)-9-hydroxy-11,15-bis(-tetrahydropyran-2-yloxy)-16-(2-cyclohexenyl)-17,18,19,20-tetranor-5,13-prostadienoic acid, (5Z,13E)-(8R,9S,11R,12R,15S,16RS)-9-hydroxy-11,15-bis(tetrahydropyran-2-yloxy)-16-methyl-16-(2-cyclopenten-1-yl)-17,18,19,20-tetranor-5,13-prostadienoic acid methyl ester, (5Z,13E)-(8R,9S,11R,12R,15S,16RS)-9-hydroxy-11,15-bis(tetrahydropyran-2-yloxy)-16,20-dimethyl-5,13-prostadien-19-ynoic acid methyl ester.

The novel intermediates of general Formula IIIa (and analogously those of Formula III) can be prepared in fully conventional fashion per se by Wittig reaction of an aldehyde of Formula VII

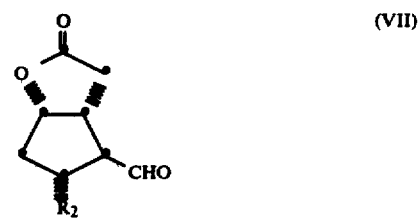
(VII)

[R$_2$=OCOPh: E. J. Corey et al. JACS 91: 5675 (1969) and E. W. Yankee et al. JACS 96: 5865 (1974)] with a phosphonate of Formula VIII

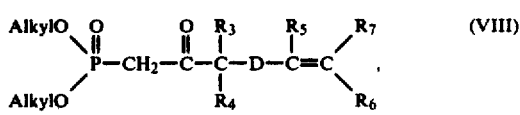
(VIII)

or with a compound of Formula IX

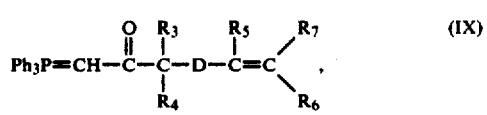
(IX)

wherein D, R$_3$, R$_4$, R$_5$, R$_6$, and R$_7$ are as defined correspondingly above, to form a ketone of Formula X

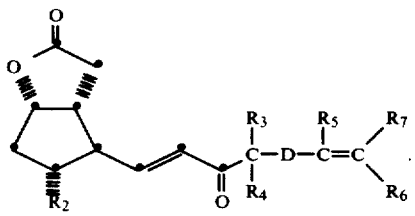

(X)

After reduction of the 15-keto group with, for example, zinc borohydride or sodium borohydride, or by reaction with alkyl magnesium bromide or alkyl lithium, the epimeric 15α- and 15β-alcohols XI (PG numbering) are obtained which, if desired, can be separated:

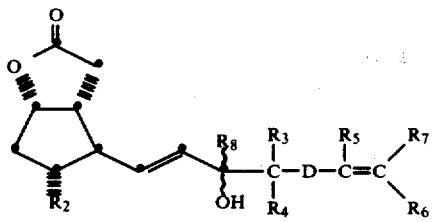

(XI)

When R$_2$ is an

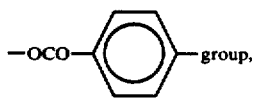

the compound can be saponified, if desired, with potassium carbonate in methanol to obtain compounds of Formula XI wherein R$_2$ is hydroxy. After blockage of the hydroxy groups present, for example with dihydrogen, a reduction is carried out with diisobutyl aluminum hydride to produce the lactol of Formula XII

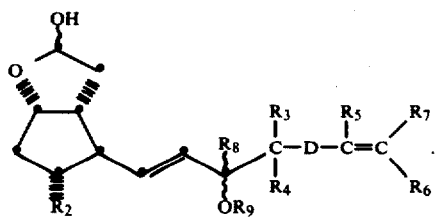

(XII)

This lactol is reacted by Wittig reaction with a phosphorane of Formula XIII

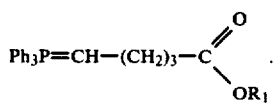

(XIII)

The already known intermediates of Formula III are described in DOS No. 2,635,985 (U.S. Pat. No. 4,235,930) and in German Patent Application P No. 30 41 602.5 and P No. 30 48 906.6, corresponding respectively to U.S. application Ser. Nos. 317,621 of Nov. 2, 1981 and 333,099 of Dec. 21, 1981, all of whose disclosures are incorporated by reference herein.

All of the intermediates of Formula III a are per se useful for the same typical PG uses disclosed above and in the latter cited documents; their administration is in accordance with conventional prostaglandins and with the foregoing disclosure.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(13E)-(11R,15S,16RS)-11,15-Dihydroxy-16,19-dimethyl-9α,6-nitrilo-13,18-prostadienoic Acid A solution of 298 mg of (5Z,13E)-(8R,9S,11R,12R,15S,16RS)-9-azido-11,15-dihydroxy-16,19-dimethyl-5,13,18-prostadienoic acid in 28 ml of ethyl acetate was stirred under argon at 80° C. for 27 hours. The mixture was then evaporated under vacuum and the residue purified by column chromatography on silica gel with ethyl acetate/0–50% methanol as the mobile phase, thus obtaining 172 mg of the title compound as a viscous oil.

IR: 3380 (broad), 2960, 2930, 2870, 1710, 1640, 1085, 1020, 970 cm$^{-1}$.

The starting material for the above title compound was prepared as follows:

1(a) 2-Ethoxycarbonyl-2,5-dimethyl-4-hexenoic Acid Ethyl Ester 36.1 g of sodium (cut into small pieces) was introduced into a three-necked flask equipped with reflux condenser, dropping funnel, and agitator. To this mixture was added 800 ml of absolute ethanol so quickly that the solution continued to boil vigorously. The hot alcoholate solution was combined dropwise with 269.6 g of freshly distilled methylmalonic acid diethyl ester, the mixture was stirred for ½ hour at 60° C. and then 241.7 g of dimethylallyl bromide was also added dropwise thereto. After one hour of agitation under heating, the thus-precipitated sodium bromide was filtered off, the precipitate was washed, and the filtrate was concentrated. The remainder was taken up in ether, washed neutral with saturated sodium chloride solution, dried over magnesium sulfate, and concentrated on a forced circulation evaporator. The evaporation residue was fractionated on an oil pump, yielding 266 g of the title compound, bp$_7$ 97°–112° C.

IR (Film): 1735, 1245, 1025, 860 cm$^{-1}$.

1(b) 2-Carboxy-2,5-dimethyl-4-hexenoic Acid 223.8 g of the diester obtained in the preceding reaction stage was heated under reflux together with 181 g of potassium hydroxide in 235 ml of water and 450 ml of ethanol for 4 hours. The ethanol was then evaporated on a forced circulation evaporator, the residue was dissolved in 235 ml of water and combined dropwise under ice cooling with concentrated hydrochloric acid until pH 1. The precipitate (mp 162°–166° C.) was collected, washed with water, and used in the subsequent stage without further purification.

IR (KBr): 1700, 1230, 840 cm$^{-1}$.

1(c) 2,5-Dimethyl-4-hexenoic Acid

The dicarboxylic acid obtained in the preceding stage was maintained in a distillation apparatus for 4 hours under normal pressure and then for one hour at 210° C. under 75 torr. The product was then distilled under vacuum, thus obtaining 68 g of the title compound (bp$_5$ 98°-106° C.; bp$_1$ 67°-70° C.).

IR (Film): 1705, 1220, 810 cm$^{-1}$.

1(d) 2,5-Dimethyl-4-hexenoic Acid Methyl Ester

The 68 g of carboxylic acid obtained as described above was combined with ethereal diazomethane solution until there was no longer any nitrogen liberation while adding the reagent, and the reaction solution assumed a permanent yellow coloring. The solvent was then removed under vacuum and the residue fractionated, yielding 62.3 g, bp$_{3.5-6}$ 32°-35° C.

IR (Film): 1735, 1160, 1050, 820 cm$^{-1}$.

1(e) 2,5-Dimethyl-4-hexenoic Acid Ethyl Ester 85.3 g of 2-ethoxycarbonyl-2,5-dimethyl-4-hexenoic acid ethyl ester was dissolved in 645 ml of dimethyl sulfoxide and combined in succession with 29.7 g of lithium chloride and 6.3 ml of distilled water. The reaction mixture was thereafter heated a total of 13 hours to 200° C. and subsequently—after cooling—poured on 1 liter of ice water. The aqueous phase was extracted three times with respectively 500 ml of methylene chloride. The combined organic extracts then were washed twice with water, dried over magnesium sulfate, concentrated on a forced circulation evaporator, and distilled under vacuum, thus isolating 53.1 g, bp$_{13}$ 75°-78° C.

IR (Film): 1735, 1160, 1050 cm$^{-1}$.

1(f) 2-(1,4-Dimethyl-3-pentenyl)-2-oxoethanephosphonic Acid Dimethyl Ester

Under argon at −60° C., 274.7 ml of a 1.61-molar butyllithium solution in hexane was added dropwise to a solution of 59 g of methanephosphonic acid dimethyl ester in 400 ml of absolute tetrahydrofuran. After 15 minutes of agitation, a solution of 34.05 g of 2,5-dimethyl-4-hexenoic acid ethyl ester in 100 ml of absolute tetrahydrofuran was added dropwise thereto. The reaction mixture was allowed to warm up to room temperature within 4 hours and thereafter stirred for another 3 hours. Then the mixture was combined with 26.5 ml of glacial acetic acid and concentrated under vacuum. The residue was taken up in ether/water, the aqueous phase was combined with solid sodium chloride, and shaken out with ether. The combined organic phases were dried over magnesium sulfate and concentrated on a forced circulation evaporator. The evaporation residue was purified by column chromatography on silica gel with hexane/50-100% ethyl acetate as the mobile phase, thus producing 32 g of the desired compound.

IR (Film): 1710, 1260, 1030 cm$^{-1}$.

1(g) (1S,5R,6R,7R)-7-Benzoyloxy-6-[(E)-(4RS)-4,7-dimethyl-3-oxo-1,6-octadienyl]-2-oxabicyclo[3,3,0]octan-3-one Under argon at room temperature, 8.4 g of the phosphonate obtained in the preceding reaction stage (dissolved in 100 ml of absolute dimethoxyethane) was added dropwise to a suspension of 1.62 g of 50% (oil-suspended) sodium hydride in 150 ml of dimethoxyethane freshly distilled over lithium aluminum hydride. After adding 1.44 g of lithium chloride (previously dried under vacuum for 2 hours at 50° C.), the reaction mixture was stirred for 2 hours at room temperature. Subsequently the suspension was cooled to −20° C. and combined within one-half hour dropwise with a solution of 9.28 g of (1S,5R,6R,7R)-6-formyl-7-benzoyloxy-2-oxabicyclo[3,3,0]octan-3-one [E. J. Corey et al., J. Amer. Chem. Soc. 91: 5675 (1969)] in 250 ml of absolute dimethoxyethane. The temperature was then allowed to rise under agitation to 0° C. within 2 hours. After controlling the reaction with analytical thin-layer chromatography, 3.4 ml of glacial acetic acid was added dropwise at −10° C. The mixture was then combined with 450 ml of water, the phases were separated, the aqueous phase was extracted three times with respectively about 200 ml of ether, the organic phases were combined and washed with 4% sodium bicarbonate solution and saturated sodium chloride solution. After drying over magnesium sulfate, the solvent was removed on a forced circulation evaporator. Purification of the residue by column chromatography on silica gel with hexane/2-0-60% ethyl acetate as the mobile phase yielded 21.1 g of the title compound as a colorless oil.

IR (Film): 1775, 1720, 1690, 1670, 1620, 1600, 1580, 1270, 1180, 710 cm$^{-1}$.

1(h) (1S,5R,6R,7R)-7-Benzoyloxy-6-[(E)-(3S,4RS)-3-hydroxy-4,7-dimethyl-1,6-octadienyl]-2-oxabicyclo[3,3,0]octan-3-one 4.8 g of sodium borohydride was added in incremental portions to a solution, cooled to −40° C., of 8.0 g of the ketone obtained in the preceding reaction stage [Example 1(g)] in 250 ml of absolute methanol. After 30 minutes of agitation at this temperature, 10.37 ml of glacial acetic acid was added—likewise at −40° C.—dropwise to the reaction solution. After removal of the solvent on a forced circulation evaporator, the residue was combined with a two-phase mixture of 200 ml of water and 300 ml of methylene chloride; the separated aqueous phase was combined with solid sodium chloride and extracted twice with respectively 200 ml of methylene chloride. The combined organic phases were washed with saturated sodium chloride solution, dried over magnesium sulfate, and concentrated under vacuum. The isomer separation of the residue was effected by column chromatography on silica gel with hexane/10-60% ethyl acetate as the mobile phase. The least polar product isolated was 4.5 g of the title compound.

IR (Film): 3480 (broad), 1775, 1720, 1605, 1590, 1280, 1180, 715 cm$^{-1}$.

1(i) (1S,5R,6R,7R)-6-[(E)-(3S)-(4RS)-3-Hydroxy-4,7-dimethyl-1,6-octadienyl]-7-hydroxy-2-oxabicyclo[3,3,0]octan-3-one A solution of 10 g of the benzoate obtained in the preceding reaction stage [Example 1(h)] in 495 ml of absolute methanol was combined with 3.5 g of potassium carbonate (anhydrous) and stirred under argon at room temperature for 5 hours. Subsequently 495 ml of 0.1 N hydrochlorid acid was added to the reaction mixture, and the latter was agitated for another 15 minutes. After concentration of the solution, the latter was extracted with ethyl acetate, the combined organic phases were then washed with saturated sodium chloride solution, dried, and evaporated to dryness. The residue was optionally purified by column chromatography on silica gel with ethyl acetate as the mobile phase.

Yield: 7.3 g of the desired compound.
IF (Film): 3460, 1765, 1180, 1030, 965 cm$^{-1}$.

1(j)
(1S,5R,6R,7R)-6-[(E)-(3S)-(4RS)-3-(Tetrahydropyran-2-yloxy)-4,7-dimethyl-1,6-octadienyl]-7-(tetrahydropyran-2-yloxy)-2-oxabicyclo[3,3,0]octan-3-one 6.52 ml of dihydropyran, freshly distilled over potassium hydroxide and 1 g of pyridine p-toluenesulfonate were added to a solution of 7.3 g of the diol obtained in the preceding reaction stage in 250 ml of absolute methylene chloride. After 21 hours of agitation at room temperature, the reaction solution was washed with semi-saturated sodium chloride solution, dried over magnesium sulfate, and concentrated under vacuum. The evaporation residue was purified by column chromatography on silica gel with ether as the mobile phase, thus obtaining 10.6 g of the title compound.

IR (Film): 1775, 1180, 1130, 1075, 1020, 970, 810 cm$^{-1}$.

1(k)
(2RS,3aR,4R,5R,6aS)-4-[(E)-(3S)-(4RS)-3-Tetrahydropyran-2-yloxy)-4,7-dimethyl-1,6-octadienyl]-5-(tetrahydropyran-2-yloxy)perhydrocyclopenta[b]furan-2-ol Uner argon, 31.2 ml of a 20% diisobutyl aluminum hydride solution in toluene was added dropwise within 10-15 minutes to a solution, cooled to −70° C., of the 10.53 g of lactone obtained in the preceding reaction stage [Example 1(j)] in 300 ml of absolute toluene. The mixture was stirred for 10 minutes, then combined dropwise with 2.21 ml of isopropanol, and at 0° C. with 16 ml of water, and the mixture was stirred for another 10 minutes. The thus-produced white granular precipitate was separated by way of a porous plate and washed with ethyl acetate. The organic phases were washed three times with saturated sodium chloride solution, dried over magnesium sulfate, and concentrated under vacuum, yielding 10.4 g of an oil used without further purification in the subsequent reaction stage.

1(l)
(5Z,13E)-(8R,9S,11R,12R,15S,16RS)-9-Hydroxy-11,15-bis(tetrahydropyran-2-yloxy)-16,19-dimethyl-5,13-18-prostatrienoic Acid 225 ml of a solution of methanesulfinylmethyl sodium in absolute dimethyl sulfoxide (solution: 15 g of 50% sodium hydride suspension in 300 ml of absolute dimethyl sulfoxide was stirred for one-half hour at 70° C.) was added dropwise at about 15° C. to a solution of 50 g of 4-carboxybutyltriphenylphosphonium bromide (dried for 1.5 hours at 75°-80° C. on an oil pump) in 200 ml of absolute dimethyl sulfoxide. After 30 minutes of agitation at room temperature, this ylene solution was added dropwise at 15° C. within 15 minutes to a solution of the 10.4 g of lactol obtained in the preceding reaction step [Example 1(k)] in 200 ml of absolute dimethyl sulfoxide and 100 ml of absolute tetrahydrofuran. Thereafter the reaction mixture as stirred for 7.5 hours at room temperature. Subsequently, the mixture was combined with about 400 ml of ice/water mixture and extracted three times with ether. The aqueous phase was adjusted to pH 4 with 10% citric acid solution and extracted respectively three times with a 1/1 mixture of ether/hexane and methylene chloride. As per analytical thin-layer chromatography, the methylene chloride phase could be discarded. The other organic phases were combined, washed three times with saturated sodium chloride solution, dried over sodium sulfate, and concentrated on a forced circulation evaporator. The residue was purified by column chromatography on silica gel with hexane/50-70% ethyl acetate as the mobile phase, thus obtaining 8.15 g of the desired carboxylic acid.

IR (Film): 3460 (broad), 2730, 2660, 1735, 1710, 1135, 1080, 1020, 975, 810 cm$^{-1}$.

1(m)
(5Z,13E)-(8R,9S,11R,12R,15S,16RS)-9-Hydroxy-11,15-bis(tetrahydropyran-2-yloxy)-16,19-dimethyl-5,13,18-prostatrienoic Acid Methyl Ester 8.15 g of the carboxylic acid obtained according to the above description [Example 1(1)] was dissolved in a small amount of methylene chloride and combined with ethereal diazomethane solution until there was no longer any gas evolution and the yellow coloring of the reaction solution became permanent. After removal of the excess diazomethane as well as the solvent under vacuum at room temperature, 8.1 g of the title compound was obtained as a colorless oil.

IR (Film): 3400 (broad), 1740, 1135, 1080, 1020, 975, 810 cm$^{-1}$.

1(n)
(5Z,13E)-(8R,9S,11R,12R,15S,16RS)-16,19-Dimethyl-11,15-bis(tetrahydropyran-2-yloxy)-9-tosyloxy-5,13,18-prostatrienoic Acid Methyl Ester A solution of 3 g of the carboxylic acid ester obtained according to Example 1(m) in 5.2 ml of dry pyridine was combined at 0° C. under argon with 2.04 g of p-toluenesulfonyl chloride and stirred for 48 hours at room temperature. After adding 2.9 ml of water, the mixture was stirred for another 2 hours at room temperature; then the reaction solution was diluted with 800 ml of ether, washed in succession with 20 ml of water, twice with respectively 30 ml of ice-cold 5% sulfuric acid, with 20 ml of water, with 30 ml of sodium bicarbonate solution, and finally with water until neutral, dried over magnesium sulfate, and concentrated to dryness under vacuum. The colorless oil was purified by column chromatography on silica gel with hexane/2-0-50% ethyl acetate as the mobile phase, thus producing 3.28 g of the title compound.

IR (Film): 2940, 2860, 1740, 1600, 1495, 1450, 1440, 1370, 1175, 1030, 1020, 970 cm$^{-1}$.

1(o)
(5Z,13E)-(8R,9R,11R,12R,15S,16RS)-9-Hydroxy-11,15-bis(tetrahydropyran-2-yloxy)-16,19-dimethyl-5,13,18-prostatrienoic Acid Methyl Ester The 3.28 g obtained in the preceding reaction stage of Example 1(n) was dissolved in 67 ml of dimethyl sulfoxide and combined with 6.8 g of potassium nitrite. After 4.5 hours of agitation at 65° C. (during which step the solution first turned green, then brown), the reaction mixture was poured into 400 ml of saturated sodium chloride solution. The mixture was then extracted five times with respectively 250 ml of ether, the combined organic phases were washed neutral with water, dried over magnesium sulfate, and concentrated to dryness under vacuum. The residue was purified by column chromatography on silica gel with ethyl acetate/hexane=1/1 as the mobile phase. Yield: 1.25 g of the desired compound as a colorless oil.

IR (Film): 3450, 2940, 2870, 1740, 1455, 1440, 1030, 1020, 970 cm$^{-1}$.

1(p)
(5Z,13E)-(8R,9R,11R,12R,15S,16RS)-16,19-Dimethyl-11,15-bis(tetrahydropyran-2-yloxy)-9-(p-toluenesulfonyloxy)-5,13,18-prostatrienoic Acid Methyl Ester At 0° C., 850 mg of p-toluenesulfonyl chloride was added to a solution of 1.25 g of the 9β-alcohol prepared in the preceding reaction stage in 2.2 ml of dry pyridine. The reaction solution was then stirred for 22 hours at room temperature under argon. After dilution with ether, the reaction mixture was then washed in succession with water, ice-cold 5% sulfuric acid, water, sodium bicarbonate solution, and once again water. The mixture was dried over magnesium sulfate, evaporated under vacuum, and the residue purified by column chromatography on silica gel with hexane/30% ethyl acetate as the mobile phase, thus obtaining 1.23 g of the title compound.

IR (Film): 2940, 2860, 1740, 1600, 1490, 1450, 1440, 1370, 1178, 1035, 1025, 970 cm$^{-1}$.

1(q)
(5Z,13E)-(8R,9R,11R,12R,15S,16RS)-11,15-Dihydroxy-16,19-dimethyl-9-(p-toluenesulfonyloxy)-5,13,18-prostatrienoic Acid Methyl Ester The 1.23 g of tosylate obtained according to Example 1(p) was stirred under argon at room temperature for 21 hours with 36 ml of a mixture of acetic acid/water/tetrahydrofuran (65/35/10). The reaction mixture was then combined with 200 ml of brine, extracted five times with respectively 150 ml of ethyl acetate, the organic phase was washed with saturated sodium bicarbonate solution and thereafter until neutral with water, dried over sodium sulfate, and concentrated under vacuum. The residue from the evaporation was subjected to column chromatography on silica gel with ethyl acetate/hexane (2/1) as the mobile phase, thus producing 766 mg of the tosylate as a colorless oil.

IR: 3400, 2950, 2920, 2870, 1735, 1595, 1495, 1450, 1435, 1360, 1175, 1095, 970 cm$^{-1}$.

1(r)
(5Z,13E)-(8R,9S,11R,12R,15S,16RS)-9-Azido-11,15-dihydroxy-16,19-dimethyl-B 5,13,18-prostatrienoic Acid Methyl Ester A solution of 752 mg of the diol produced according to Example 1(q) in 16.5 ml of hexamethylphosphoric triamide was combined with 161 mg of sodium azide and agitated for 4.5 hours at 40° C. The cooled-off reaction mixture was combined with 100 ml of ice water, extracted five times with respectively 50 ml of ether, the organic phase was washed three times with sodium chloride solution, dried over magnesium sulfate, and concentrated under vacuum. The thus-obtained title compound, an oil which was uniform as determined by thin-layer chromatography, was used without further purification in the subsequent reaction.

IR: 3380, 2960, 2930, 2870, 2100, 1740, 1450, 1435, 970 cm$^{-1}$.

1(s)
(5Z,13E)-(8R,9S,11R,12R,15S,16RS)-9-Azido-11,15-dihydroxy-16,19-dimethyl-5,13,18-prostatrienoic Acid The azide obtained according to Example 1(r) was introduced into 13.7 ml of a solution of 3.6 g of potassium hydroxide, 24 ml of water, and 120 ml of methanol, and stirred for 4 hours at room temperature under argon. The reaction mixture was then introduced into 40 ml of water and washed once with ether/hexane (1/1); the aqueous phase was thereafter cooled to 5° C., acidified to pH 6 with 10% citric acid solution, and extracted five times with respectively 50 ml of methylene chloride. The combined organic phases were washed with 100 ml of saturated sodium chloride solution, dried over magnesium sulfate, and concentrated under vacuum. The evaporation residue was subjected to purification by column chromatography on silica gel with ethyl acetate/0–5% methanol as the mobile phase, thus obtaining 298 mg of the title compound as a colorless oil.

IR: 3400 (broad), 2950, 2930, 2875, 2120, 1710, 1450, 1435, 970 cm$^{-1}$.

EXAMPLE 2
(13E)-(11R,15R,16RS)-11,15-Dihydroxy-16,19-dimethyl-9α,6-nitrilo-13,18-prostadienoic Acid A solution of 340 mg of (5Z,13E)-(8R,9S,11R,12R,15R,16RS)-9-azido-11,15-dihydroxy-16,19-dimethyl-5,13,18-prostatrienoic acid in 32 ml of ethyl acetate was stirred at 80° C. under argon for 26 hours. The mixture was then concentrated under vacuum and the residue purified by column chromatography on silica gel with ethyl acetate/0–40% methanol as the mobile phase, thus obtaining 205 mg of the title compound as a colorless oil.

IR: 3400 (broad), 2960, 2920, 2870, 1710, 1640, 1085, 1020, 970 cm$^{-1}$.

The starting material for the above title compound was produced as described below:

2(a)
(1S,5R,6R,7R)-7-Benzoyloxy-6-[(E)-(3R,4RS)-3-hydroxy-4,7-dimethyl-1,6-octadienyl]-2-oxabicyclo[3,3,0]octan-3-one In the sodium borohydride reaction of the ketone of Example 1(g), 2.3 g of the title compound was isolated as the polar product in addition to the 4.5 g of 15α-alcohol [Example 1(h)], as well as 0.34 g of 2β-mixture.

IR (Film): 3480 (broad), 1770, 1715, 1600, 1580, 1275, 1180, 710 cm$^{-1}$.

2(b)
(1S,5R,6R,7R)-6-[(E)-(3R)-(4RS)-3-Hydroxy-4,7-dimethyl-1,6-octadienyl]-7-hydroxy-2-oxabicyclo[3,3,0]octan-3-one Analogously to the directions given for the benzoate splitting step in connection with the 15α-hydroxy isomer [Example 1(i)], 4.58 g of the ester obtained in the preceding reaction stage was reacted with 1.6 g of anhydrous potassium carbonate, thus obtaining 3.27 g of diol.

IR (Film): 3460, 1770, 1180, 1035, 965 cm$^{-1}$.

2(c)
(1S,5R,6R,7R)-6-[(E)-(3R)-(4RS)-3-(Tetrahydropyran-2-yloxy)-4,7-dimethyl-1,6-octadienyl]-7-(tetrahydropyran-2-yloxy)-2-oxabicyclo[3,3,0]octan-3-one In correspondence with the directions given for the ether formation of the 15α-hydroxy isomer [Example 1(j)], 3.27 g of the diol obtained in the preceding stage was reacted with 2.93 ml of dihydropyran and 455 mg of pyridine-p-toluenesulfonate. After a reaction period of 25 hours and after column chromatography on silica gel with ether as the mobile phase, 4.3 g of the title compound was obtained as a colorless oil.

IR (Film): 1775, 1180, 1130, 1075, 1020, 970, 810 cm$^{-1}$.

2(d)
(2RS,3aR,4R,5R,6aS)-4-[(E)-(3R)-(4RS)-3-(Tetrahydropyran-2-yloxy)-4,7-dimethyl-1,6-octadienyl]-5-(tetrahydropyran-2-yloxy)perhydrocyclopenta[b]furan-2-ol The 4.3 g of lactone obtained in the preceding reaction stage was reacted analogously to the directions given for preparing the isomeric 15α-lacton [Example 1(k)] with 12.7 ml of 20% diisobutyl aluminum hydride solution, thus producing 4.25 g of lactol used without further purification in the subsequent stage.

2(e)
(5Z,13E)-(8R,9S,11R,12R,15R,16RS)-9-Hydroxy-11,15-bis(tetrahydropyran-2-yloxy)-16,19-dimethyl-5,13,18-prostatrienoic Acid The 4.25 g obtained in the preceding reaction stage was reacted analogously to the directions for producing the corresponding 16α-isomer [Example 1(l)] with 20.35 g of 4-carboxybutyltriphenylphosphonium bromide and 88.5 ml of methanesulfinylmethyl sodium, thus obtaining 3.2 g of carboxylic acid.

IR (Film): 3460 (broad), 2725, 2660, 1735, 1705, 1130, 1080, 1020, 975, 810 cm$^{-1}$.

2(f)
(5Z,13E)-(8R,9S,11R,12R,15R,16RS)-9-Hydroxy-11,15-bis(tetrahydropyran-2-yloxy)-16,19-dimethyl-5,13,18-prostatrienoic Acid Methyl Ester Analogously to the method described for preparation of the 15α-isomer [Example 1(m)], the 3.2 g of carboxylic acid of Example 2(e) were reacted, thus obtaining 3.15 g of ester.

IR (Film): 3400 (broad), 1740, 1135, 1080, 1020, 975, 810 cm$^{-1}$.

2(g)
(5Z,13E)-(8R,9S,11R,12R,15R,16RS)-16,19-Dimethyl-11,15-bis(tetrahydropyran-2-yloxy)-9-tosyloxy-5,13,18-prostatrienoic Acid Methyl Ester A solution of 3.15 g of the carboxylic acid ester produced according to Example 2(f) in 5.5 ml of dry pyridine was combined at 0° C. and under argon with 2.14 g of p-toluenesulfonyl chloride and stirred for 50 hours at room temperature. After adding 3 ml of water, the mixture was agitated for another 2 hours at room temperature. Subsequently, the reaction solution was diluted with 800 ml of ether, washed in succession with 20 ml of water, twice with respectively 30 ml of ice-cold 5% sulfuric acid, with 20 ml of water, with 30 ml of sodium bicarbonate solution and finally with water until neutral, dried over magnesium sulfate, and concentrated to dryness under vacuum. The colorless oil was purified by column chromatography on silica gel with hexane/20–50% ethyl acetate as the mobile phase, thus obtaining 3.7 g of the title compound.

IR (Liquid Film): 2940, 2850, 1740, 1600, 1490, 1450, 1440, 1360, 1170, 1030, 1020, 970 cm$^{-1}$.

2(h)
(5Z,13E)-(8R,9R,11R,12R,15R,16RS)-9-Hydroxy-11,15-bis(tetrahydropyran-2-yloxy)-16,19-dimethyl-5,13,18-prostatrienoic Acid Methyl Ester The 3.7 g obtained in the preceding reaction stage [Example 2(g)] was dissolved in 75 ml of dimethyl sulfoxide and combined with 7.6 g of potassium nitrite. After 4.5 hours of agitation at 65° C. (during which step the solution first turned green, then brown), the reaction mixture was poured into 400 ml of saturated sodium chloride solution. The mixture was then extracted five times with respectively 250 ml of ether, the combined organic phases were washed neutral with water, dried over magnesium sulfate, and concentrated to dryness under vacuum. The residue was purified by column chromatography on silica gel with ethyl acetate/hexane = 1/1 as the mobile phase. Yield: 1.5 g of the title compound as a colorless oil.

IR: 3400, 2940, 2860, 1740, 1455, 1440, 1030, 1020, 970 cm$^{-1}$.

2(i)
(5Z,13E)-(8R,9R,11R,12R,15R,16RS)-16,19-Dimethyl-11,15-bis(tetrahydropyran-2-yloxy)-9-(p-toluenesulfonyloxy)-5,13,18-prostatrienoic Acid Methyl Ester At 0° C., 1 g of p-toluenesulfonyl chloride was added to a solution of 1.5 g of the 9β-alcohol prepared in the preceding reaction stage in 2.6 ml of dry pyridine. The reaction solution was then stirred for 22 hours at room temperature under argon. After dilution with ether, the reaction mixture was then washed in succession with water, ice-cold 5% sulfuric acid, water, sodium bicarbonate solution, and once again water, dried over magnesium sulfate, evaporated under vacuum, and the residue purified by column chromatography on silica gel with hexane/30% ethyl acetate as the mobile phase, thus obtaining 1.5 g of the title compound.

IR (Film): 2940, 2860, 1740, 1600, 1495, 1450, 1440, 1370, 1170, 1030, 1020, 970 cm$^{-1}$.

2(j)
(5Z,13E)-(8R,9R,11R,12R,15R,16RS)-11,15-Dihydroxy-16,19-dimethyl-9-(p-toluenesulfonyloxy)-5,13,18-prostatrienoic Acid Methyl Ester The 1.5 g of tosylate obtained according to Example 2(i) was stirred for 21 hours with 4.5 ml of a mixture of acetic acid/water/tetrahydrofuran (65/35/10) under argon at room temperature. Thereafter the reaction mixture was combined with 200 ml of brine, extracted five times with respectively 150 ml of ethyl acetate, the organic phase was washed with saturated sodium bicarbonate solution and thereafter neutral with water, dried over sodium sulfate, and concentrated under vacuum. The evaporation residue was subjected to column chromatography on silica gel with ethyl acetate/hexane = 2/1 as the mobile phase, thus obtaining 910 mg of the tosylate.

IR (Film): 3400, 2950, 2920, 2870, 1740, 1595, 1490, 1450, 1435, 1360, 1175, 1090, 970 cm$^{-1}$.

2(k)
(5Z,13E)-(8R,9S,11R,12R,15R,16RS)-9-Azido-11,15-dihydroxy-16,19-dimethyl-5,13,18-prostatrienoic Acid Methyl Ester A solution of 900 mg of the diol produced according to Example 2(j) in 20 ml of hexamethylphosphoric triamide was combined with 190 mg of sodium azide and agitated for 4.5 hours at 40° C. The cooled-off reaction mixture was combined with 100 ml of ice water, extracted five times with respectively 50 ml of ether, the organic phase washed three times with sodium chloride solution, dried over magnesium sulfate, and concentrated under vacuum. The title compound, obtained in this way as an oil uniform as per thin-layer chromatography, was utilized in the subsequent reaction without further purification.

IR (Film): 3400, 2960, 2930, 2870, 2100, 1740, 1450, 1430, 970 cm$^{-1}$.

2(l)
(5Z,13E)-(8R,9S,11R,12R,15R,16RS)-9-Azido-11,15-dihydroxy-16,19-dimethyl-5,13,18-prostatrienoic Acid The azide produced according to Example 2(k) was introduced into 16.4 ml of a solution of 3.6 g of potassium hydroxide, 24 ml of water, and 120 ml of methanol and agitated under argon at room temperature for 4 hours. Then the reaction mixture was poured into 40 ml of water and washed once with ether/hexane=1/1; the aqueous phase was thereafter cooled to 5° C., acidified with 10% citric acid solution to pH 6 and extracted five times with respectively 50 ml of methylene chloride. The combined organic phases were washed with 100 ml of saturated sodium chloride solution, dried over magnesium sulfate, and concentrated under vacuum. The residue from the evaporation was purified by column chromatography on silica gel with ethyl acetate/0–5% methanol as the mobile phase, thus obtaining 340 mg of the title compound.

IR (Film): 3400 (broad), 2950, 2930, 2870, 2120, 1710, 1450, 1430, 970 cm$^{-1}$.

EXAMPLE 3
(13E)-(11R,15S)-11,15-Dihydroxy-16,16,19-trimethyl-9α,6-nitrilo-13,18-prostadienoic Acid A solution of 210 mg of (5Z,13E)-(8R,9S,11R,12R,15S)-9-azido-11,15-dihydroxy-16,16,19-trimethyl-5,13,18-prostatrienoic acid in 18 ml of ethyl acetate was stirred under argon at 80° C. for 27 hours. The mixture was then evaporated under vacuum and the residue purified by column chromatography on silica gel with ethyl acetate/0–50% methanol as the mobile phase, thus producing 130 mg of the title compound as a colorless oil.

IR: 3400 (broad), 2960, 2920, 2875, 1705, 1640, 1085, 1020, 975 cm$^{-1}$.

The starting material for the above title compound was prepared as follows:

3(a) 2,2,5-Trimethyl-4-hexenoic Acid Ethyl Ester

A solution of 101.2 g of diisopropylamine in 125 ml of absolute tetrahydrofuran was combined under argon at −20° C. dropwise with 610 ml of a 1.64 N butyllithium solution in hexane. The temperature was allowed to rise for a short time to about 0° C. and then, at −50° to −60° C., 116 g of ethyl isobutyrate was added dropwise to the lithium diisopropylamide solution. The reaction solution was stirred for one hour at 0° C., then cooled to −40° C. and thereafter added to a solution of 200 g of 4-bromo-2-methyl-2-butene (dimethylallyl bromide) in 60 ml of absolute dimethyl sulfoxide, maintained at −20° C. While allowing the temperature to rise to room temperature, the reaction mixture was agitated for 60 hours and then combined with 250 ml of saturated sodium chloride solution. The organic phase was separated, and the aqueous phase was extracted five times with respectively 200 ml of a 1/1 mixture of ether and hexane. The combined organic phases were washed neutral with 0.5 N hydrochloric acid and saturated sodium chloride solution, dried over magnesium sulfate, and concentrated on a forced circulation evaporator. The residue was distilled under vacuum, thus obtaining 91.5 g of the desired ester, bp$_{13}$ 76°–81° C.

IR (Film): 1735, 1160, 1060, 820 cm$^{-1}$.

3(b) 2,2,5-Trimethyl-4-hexenoic Acid Methyl Ester

This compound was produced according to the above description for the synthesis of the corresponding ethyl ester; bp$_{13}$ 72°–74° C.

IR (Film): 1735, 1160, 1050, 820 cm$^{-1}$.

3(c) 2,2,5-Trimethyl-4-hexenoic Acid

This compound was produced according to the above directions with isobutyric acid as the educt, as well as 2 equivalents of lithium diisopropylamide; bp$_{0.2-0.4}$ 94°–100° C.

IR (Film): 1705, 1220, 820 cm$^{-1}$.

3(d)
2-(1,1,4-Trimethyl-3-pentenyl)-2-oxoethanephosphonic Acid Dimethyl Ester Under argon at −60° C., 49.5 ml of a 2.02 N butyllithium solution in hexane was added dropwise to a solution of 13 g of methanephosphonic acid dimethyl ester in 160 ml of absolute tetrahydrofuran. After 15 minutes, a solution of 9.2 g of 2,2,5-trimethyl-4-hexenoic acid ethyl ester in 25 ml of absolute tetrahydrofuran was added dropwise thereto. After 2 hours at −60° C., the reaction mixture was allowed to warm up to room temperature within one hour, combined with 5.72 ml of glacial acetic acid, and then concentrated under vacuum. The residue, a white, gel-like mass, was distributed in a two-phase mixture of 35 ml of water and 165 ml of ether. The organic phase was dried over magnesium sulfate and concentrated on a forced circulation evaporator. After removing the volatile byproducts by distillation under 0.1 torr and at 60° C., the residue was purified by column chromatography on silica gel with hexane/50–100% ethyl acetate as the mobile phase, thus obtaining 8.6 g of the title compound.

IR (Film): 1705, 1260, 1030, 800 cm$^{-1}$.

3(e)
(1S,5R,6R,7R)-7-Benzoyloxy-6-[(E)-4,4,7-trimethyl-3-oxo-1,6-octadienyl]-2-oxabicyclo[3,3,0]octan-3-one Under argon at room temperature, 6.06 g of the phosphonate obtained in the preceding reaction stage (dissolved in 60 ml of absolute dimethoxyethane) was added dropwise to a suspension of 1.1 g of 50% (oil-suspended) sodium hydride in 120 ml of dimethoxyethane freshly distilled over lithium aluminum hydride. After adding 0.98 g of lithium chloride (previously dried under vacuum for 2 hours at 50° C.), the reaction mixture was stirred at room temperature for 2 hours. Subsequently the suspension was cooled to −20° C. and combined dropwise within one-half hour with a solution of 6.34 g of (1S,5R,6R,7R)-6-formyl-7-benzoyloxy-2-oxabicyclo[3,3,0]octan-3-one [E. J. Corey et al., J. Amer. Chem. Soc. 91: 5675 (1969)] in 180 ml of absolute dimethoxyethane. The temperature was then allowed to rise within 2 hours under agitation to 0° C. After controlling the reaction by analytical thin-layer chromatography, 2.3 ml of glacial acetic acid was then added dropwise at −10° C. The mixture was combined with 350 ml of water, the phases were separated, the aqueous phase was extracted three times with respectively about 200 ml of ether, the organic phases were combined and washed with 4% sodium bicarbonate solution and saturated sodium chloride solution. After drying over magnesium sulfate, the solvent was removed on a forced circulation evaporator. Purification of the residue by column chromatography on silica gel with hexane/20–40% ethyl acetate as the mobile phase yielded 5.58 g of the title compound as a colorless oil, mp 98° C.

IR (KBr): 1775, 1720, 1690, 1625, 1600, 1580, 1275, 1180, 710 cm$^{-1}$.

3(f)
(1S,5R,6R,7R)-7-Benzoyloxy-6-[(E)-(3R)-3-hydroxy-4,4,7-trimethyl-1,6-octadienyl]-2-oxabicyclo[3,3,0]octan-3-one 6.9 g of sodium borohydride was added in incremental portions to a solution, cooled to −40° C., of 11.9 g of the ketone obtained in the preceding reaction stage [Example 3(e)] in a mixture of 360 ml of methanol and 180 ml of tetrahydrofuran. After 2.5 hours—likewise at −40° C.—15 ml of glacial acetic acid was added dropwise to the reaction solution under vigorous foaming. After removing the solvent on a forced circulation evaporator, the residue was taken up in methylene chloride, washed with saturated sodium chloride solution, dried over magnesium sulfate, and concentrated under vacuum. The separation of isomers was accomplished by column chromatography on silica gel with hexane/10–40% ethyl acetate as the mobile phase, thus isolating 4.1 g of the title compound as the least polar product.

IR (KBr): 3500 (broad), 1760, 1750, 1720, 1600, 1580, 1275, 1175, 710 cm$^{-1}$.

3(g)
(1S,5R,6R,7R)-6-[(E)-(3R)-3-Hydroxy-4,4,7-trimethyl-1,6-octadienyl]-7-hydroxy-2-oxabicyclo[3,3,0]octan-3-one A solution of 8.2 g of the benzoate obtained in the preceding reaction stage [Example 3(f)] in 395 ml of absolute methanol was combined with 2.8 g of potassium carbonate (anhydrous) and stirred for 2.5 hours at room temperature under argon. Thereafter 395 ml of 0.1 N hydrochloric acid was added to the reaction mixture and the latter was stirred for another 15 minutes. After concentrating the solution, the latter was extracted with ethyl acetate, the combined organic phases were then washed with saturated sodium chloride solution, dried and evaporated to dryness. The residue was purified by column chromatography on silica gel with hexane/10–100% ethyl acetate as the mobile phase, thus producing 4.75 g of the title compound.

IR (KBr): 3410 (broad), 1760, 1180, 1035, 965 cm$^{-1}$.

3(h)
(1S,5R,6R,7R)-6-[(E)-(3R)-3-(Tetrahydropyran-2-yloxy)-4,4,7-trimethyl-1,6-octadienyl]-7-(tetrahydropyran-2-yloxy)-2-oxabicyclo[3,3,0]octan-3-one At 0° C., 17 ml of dihydropyran, freshly distilled over potassium hydroxide, and 42 mg of p-toluenesulfonic acid were added to a solution of 4.75 g of the diol obtained in the preceding reaction stage in 250 ml of absolute methylene chloride. After 40 minutes of agitation at this temperature, the reaction solution was washed three times with saturated sodium bicarbonate solution and then with saturated sodium chloride solution, dried over magnesium sulfate, and evaporated under vacuum. The evaporation residue was purified by column chromatography on silica gel with hexane/50–100% ether as the mobile phase, thus obtaining 6.9 g of the desired compound.

IR (Film): 1780, 1180, 1120, 1080, 1020, 975, 815 cm$^{-1}$.

3(i)
(2RS,3aR,4R,5R,6aS)-4-[(E)-(3R)-3-(Tetrahydropyran-2-yloxy)-4,4,7-trimethyl-1,6-octadienyl]-5-(tetrahydropyran-2-yloxy)-perhydrocyclopenta[b]furan-2-ol Under argon, 20 ml of a 20% diisobutyl aluminum hydride solution in toluene was added dropwise within 10–15 minutes to a solution, cooled to −65° C., of the 6.9 g of lactone obtained in the preceding reaction stage in 150 ml of absolute toluene. The mixture was stirred for 20 minutes, then 1 ml of isopropanol and, at 0° C., 22 ml of water were added dropwise thereto, and the mixture was stirred for another 10 minutes. The resultant white, grainy precipitate was separated by way of a porous filter and washed with ethyl acetate. The organic phases were washed three times with saturated sodium chloride solution, dried over magnesium sulfate, and concentrated under vacuum, thus producing 7.1 g of an oil used without further purification in the subsequent reaction stage.

3(j)
(5Z,13E)-(8R,9S,11R,12R,15R)-9-Hydroxy-11,15-bis(-tetrahydropyran-2-yloxy)-16,16,19-trimethyl-5,13,18-prostatrienoic Acid At about 15° C., 139 ml of a solution of methanesulfinylmethyl sodium in absolute dimethyl sulfoxide (solution: 10 g of 50% sodium hydride suspension in 200 ml of absolute dimethyl sulfoxide is stirred for one-half hour at 70° C.) was added dropwise to a solution of 32 g of 4-carboxybutyltriphenylphosphonium bromide (dried for 1.5 hours on an oil pump at 75°–80° C.) in 200 ml of absolute dimethyl sulfoxide. After 30 minutes of agitation at room temperature, this ylene solution was added dropwise at 15° C. within 15 minutes to a solution of the 7.1 g of lactol obtained in the preceding reaction step in 100 ml of absolute dimethyl sulfoxide, whereafter the reaction mixture was agitated for 3 hours at 45° C. Subsequently, the mixture was combined with 500 ml of ice/water mixture and extracted three times with ether. The aqueous phase was adjusted to pH 4 with 10% citric acid solution and extracted respectively three times with a 1/1 mixture of ether/hexane and methylene chloride. As per analytical thin-layer chromatography, the methylene chloride phase could be discarded. The other organic phases were combined, washed three times with saturated sodium chloride solution, dried over sodium sulfate, and concentrated on a forced circulation evaporator. The residue was purified by column chromatography on silica gel with hexane/50–100% ether as the mobile phase, thus obtaining 1.9 g of the desired carboxylic acid.

IR (Film): 3460 (broad), 2720, 2640, 1735, 1705, 1130, 1075, 1020, 970, 805 cm$^{-1}$.

3(k)
(5Z,13E)-(8R,9S,11R,12R,15R)-9-Hydroxy-11,15-bis(-tetrahydropyran-2-yloxy)-16,16,19-trimethyl-5,13,18-prostatrienoic Acid Methyl Ester 1.9 g of the carboxylic acid obtained according to the preceding directions was dissolved in 36 ml of methylene chloride and combined with such an amount of ethereal diazomethane solution until there was no longer any liberation of gas and the reaction solution assumed a permanent yellow color. After removal of the excess diazomethane as well as the solvent under vacuum at room temperature and purification of the residue by column chromatography on silica gel with hexane/50–100% ethyl acetate as the mobile phase, 1.92 g of the title compound was obtained as a colorless oil.

IR (Film): 3400 (broad), 1735, 1135, 1070, 1020, 970, 810 cm$^{-1}$.

3(l)
(5Z,13E)-(8R,9S,11R,12R,15S)-16,16,19-Trimethyl-11,15-bis(tetrahydropyran-2-yloxy)-9-tosyloxy-5,13,18-prostatrienoic Acid Methyl Ester A solution of 2.3 g of the carboxylic acid methyl ester obtained in the preceding reaction stage [Example 3(k)] in 3.9 ml of dry pyridine was combined under argon at 0° C. with 2.5 g of p-toluenesulfonyl chloride and agitated at room temperature for 50 hours. After the addition of 2.2 ml of water, the mixture was stirred at room temperature for another 2 hours, whereupon the reaction solution was diluted with 600 ml of ether, washed in succession with 20 ml of water, twice with respectively 30 ml of ice-cold 5% sulfuric acid, with 20 ml of water, with 30 ml of sodium bicarbonate solution and then until neutral with water, dried over magnesium sulfate, and evaporated to dryness under vacuum. Purification of the colorless oil by column chromatography on silica gel with hexane/30–50% ethyl acetate as the mobile phase yielded 2.3 g of the title compound.

IR (Liquid Film): 2940, 2880, 1740, 1600, 1493, 1450, 1440, 1370, 1170, 1030, 1020, 975 cm$^{-1}$.

3(m)
(5Z,13E)-(8R,9R,11R,12R,15S)-9-Hydroxy-11,15-bis(-tetrahydropyran-2-yloxy)-16,16,19-trimethyl-5,13,18-prostatrienoic Acid Methyl Ester The 2.3 g obtained in the preceding reaction stage according to Example 3(l) was dissolved in 50 ml of dimethyl sulfoxide and combined with 4.8 g of potassium nitrite. After 4.5 hours of agitation at 65° C. (during which step the solution first turned green, then brown), the reaction mixture was poured into 300 ml of saturated sodium chloride solution. The mixture was then extracted five times with respectively 250 ml of ether, the combined organic phases were washed neutral with water, dried over magnesium sulfate, and concentrated to dryness under vacuum. The residue was purified by column chromatography on silica gel with ethyl acetate/hexane=1/1 as the mobile phase, thus obtaining 910 mg of the desired compound as a colorless oil.

IR (Film): 3400, 2950, 2870, 1740, 1450, 1440, 1030, 1020, 975 cm$^{-1}$.

3(n)
(5Z,13E)-(8R,9R,11R,12R,15S)-16,16,19-Trimethyl-11,15-bis(tetrahydropyran-2-yloxy)-9-(p-toluenesulfonyloxy)-5,13,18-prostatrienoic Acid Methyl Ester At 0° C., 600 mg of p-toluenesulfonyl chloride was added to a solution of 910 mg of the 9β-alcohol produced in the preceding reaction stage in 1.5 ml of dry pyridine. The reaction solution was then stirred under argon at room temperature for 21 hours. After dilution with ether, the reaction mixture was washed in succession with water, ice-cold 5% sulfuric acid, water, sodium bicarbonate solution and again water, dried over magnesium sulfate, evaporated under vacuum, and the residue purified by column chromatography on silica gel with hexane/30% ethyl acetate as the mobile phase, thus obtaining 810 mg of the title compound.

IR: 2960, 2870, 1740, 1600, 1490, 1450, 1440, 1370, 1175, 1030, 1020, 975 cm$^{-1}$.

3(o)
(5Z,13E)-(8R,9R,11R,12R,15S)-11,15-Dihydroxy-16,16,19-trimethyl-9-(p-toluenesulfonyloxy)-5,13,18-prostatrienoic Acid Methyl Ester The 810 mg of 9β-tosylate obtained according to Example 3(n) was stirred for 22 hours with 23 ml of a mixture of acetic acid/water/tetrahydrofuran (65/35/10) under argon at room temperature. The reaction mixture was then combined with 150 ml of saturated sodium chloride solution, extracted three times with respectively 100 ml of ethyl acetate, the organic phase was washed with saturated sodium bicarbonate solution and thereafter until neutral with water, dried over sodium sulfate, and concentrated under vacuum. The evaporation residue was subjected to column chromatography on silica gel with ethyl acetate/hexane=2/1 as the mobile phase, thus producing 500 mg of the tosylate as a colorless oil.

IR: 3400 (broad), 2950, 2920, 2860, 1740, 1595, 1495, 1450, 1435, 1360, 1175, 1095, 975 cm$^{-1}$.

3(p)
(5Z,13E)-(8R,9S,11R,12R,15S)-9-Azido-11,15-dihydroxy-16,16,19-trimethyl-5,13,18-prostatrienoic Acid Methyl Ester A solution of 500 mg of the diol produced according to Example 3(o) in 10.5 ml of hexamethylphosphoric triamide was combined with 105 mg of sodium azide and stirred for 4.5 hours at 40° C. The cooled-off reaction mixture was combined with 100 ml of ice water, extracted five times with respectively 50 ml of ether, the organic phase was washed three times with sodium chloride solution, dried over magnesium sulfate, and evaporated under vacuum. The title compound obtained in this way as an oil, uniform as per thin-layer chromatography, was used in the subsequent reaction stage without further purification.

IR: 3400 (broad), 2960, 2930, 2870, 2100, 1735, 1450, 1435, 975 cm$^{-1}$.

3(q)
(5Z,13E)-(8R,9S,11R,12R,15S)-9-Azido-11,15-dihydroxy-16,16,19-trimethyl-5,13,18-prostatrienoic Acid The azide obtained in the preceding reaction stage [Example 3(p)] was introduced into 8.9 ml of a solution of 3.6 g of potassium hydroxide, 24 ml of water, and 120 ml of methanol and stirred under argon at room temperature for 4 hours. The reaction solution was then poured into 40 ml of water and washed once with ether/hexane=1/1; the aqueous phase was then cooled to 5° C., acidified with 10% citric acid solution to pH 6, and extracted five times with respectively 50 ml of methylene chloride. The combined organic phases were washed with 100 ml of saturated sodium chloride solution, dried over magnesium sulfate, and concentrated under vacuum. The evaporation residue was subjected to purification by column chromatography on silica gel with ethyl acetate/0–5% methanol as the mobile phase, thus obtaining 210 mg of the title compound as a colorless oil.

IR: 3400 (broad), 2950, 2920, 2875, 2120, 1705, 1450, 1430, 975 cm$^{-1}$.

EXAMPLE 4

(13E)-(11R,15S)-11,15-Dihydroxy-19-methyl-9α,6-nitrilo-13,18-prostadienoic Acid

A solution of 180 mg of (5Z,13E)-(8R,9S,11R,12R,15S)-9-azido-11,15-dihydroxy-19-methyl-5,13,18-prostatrienoic acid in 18 ml of ethyl acetate was agitated under argon at 80° C. for 25 hours. Then the mixture was evaporated under vacuum and the residue purified by column chromatography on silica gel with ethyl acetate/5–50% methanol as the mobile phase, thus producing 90 mg of the title compound as a viscous oil.

IR: 3400 (broad), 2950, 2930, 2870, 1710, 1640, 1080, 1020, 975 cm$^{-1}$.

The starting material for the above title compound was prepared as follows:

4(a)

(5Z,13E)-(8R,9S,11R,12R,15S)-19-Methyl-11,15-bis(-tetrahydropyran-2-yloxy)-9-tosyloxy-5,13,18-prostatrienoic Acid Methyl Ester A solution of 1.65 g of (5Z,13E)-(8R,9S,11R,15S)-9-hydroxy-11,15-bis(tetrahydropyran-2-yloxy)-19-methyl-5,13,18-prostatrienoic acid methyl ester (produced from the corresponding acid with ethereal diazomethane solution) in 2.9 ml of dry pyridine was combined at 0° C. under argon with 1.16 g of p-toluenesulfonyl chloride and stirred for 50 hours at room temperature. After adding 1.6 ml of water, the mixture was agitated for another 2 hours at room temperature, whereafter it was diluted with 450 ml of ether, washed in succession with 20 ml of water, twice with respectively 30 ml of ice-cold 5% sulfuric acid, with 20 ml of water, with 30 ml of sodium bicarbonate solution, and then neutral with water, dried over magnesium sulfate, and evaporated to dryness under vacuum. The colorless oil was purified by column chromatography on silica gel with hexane/30–50% ethyl acetate as the mobile phase, thus obtaining 1.7 g of the title compound.

IR (Liquid Film): 2960, 2880, 1735, 1605, 1493, 1450, 1440, 1370, 1175, 1030, 1020, 975 cm$^{-1}$.

4(b)

(5Z,13E)-(8R,9R,11R,12R,15S)-9-Hydroxy-11,15-bis(-tetrahydropyran-2-yloxy)-19-methyl-5,13,18-prostatrienoic Acid Methyl Ester The 1.7 g obtained in the preceding reaction stage according to Example 4(a) was dissolved in 36 ml of dimethyl sulfoxide and combined with 3.6 g of potassium nitrite. After 4 hours of agitation at 65° C. (during which step the solution first turned green, then brown), the reaction mixture was poured into 300 ml of saturated sodium chloride solution, whereafter the mixture was extracted five times with respectively 250 ml of ether, the combined organic phases washed with water until neutral, dried over magnesium sulfate, and evaporated under vacuum to dryness. The residue was purified by column chromatography on silica gel with ethyl acetate/hexane=1/1 as the mobile phase, thus obtaining 700 mg of the desired compound as a colorless oil.

IR: 3400, 2960, 2870, 1735, 1450, 1440, 1030, 1020, 975 cm$^{-1}$.

4(c)

(5Z,13E)-(8R,9R,11R,12R,15S)-19-Methyl-11,15-bis(-tetrahydropyran-2-yloxy)-9-(p-toluenesulfonyloxy)-5,13,18-prostatrienoic Acid Methyl Ester At 0° C., 500 mg of p-toluenesulfonyl chloride was added to a solution of 700 mg of the 9β-alcohol produced in the preceding reaction stage in 1.3 ml of dry pyridine. The reaction solution was then stirred under argon at room temperature for 20 hours. After dilution with ether, the reaction mixture was washed in succession with water, ice-cold 5% sulfuric acid, water, sodium bicarbonate solution, and again with water, dried over magnesium sulfate, evaporated under vacuum, and the residue purified by column chromatography on silica gel with hexane/20% ethyl acetate as the mobile phase, thus obtaining 700 mg of the title compound.

IR: 2960, 2870, 1735, 1600, 1490, 1450, 1440, 1370, 1175, 1030, 1020, 975 cm$^{-1}$.

4(d)

(5Z,13E)-(8R,9R,11R,12R,15S)-11,15-Dihydroxy-19-methyl-9-(p-toluenesulfonyloxy)-5,13,18-prostatrienoic Acid Methyl Ester The 700 mg of 9β-tosylate obtained according to Example 4(c) was stirred for 20 hours with 21 ml of a mixture of acetic acid/water/tetrahydrofuran (65/35/10) under argon at room temperature. The reaction mixture was then combined with 150 ml of saturated sodium chloride solution, extracted three times with respectively 100 ml of ethyl acetate, the organic phase was washed with saturated sodium bicarbonate solution and thereafter neutral with water, dried over sodium sulfate, and concentrated under vacuum. The evaporation residue was subjected to column chromatography on silica gel with ethyl acetate/hexane=2/1 as the mobile phase, thus obtaining 460 mg of the tosylate as a colorless oil.

IR: 3400 (broad), 2950, 2920, 2870, 1735, 1600, 1495, 1450, 1435, 1360, 1175, 1095, 975 cm$^{-1}$.

4(e)

(5Z,13E)-(8R,9S,11R,12R,15S)-9-Azido-11,15-dihydroxy-19-methyl-5,13,18-prostatrienoic Acid Methyl Ester A solution of 460 mg of the diol produced according to Example 4(d) in 10 ml of hexamethylphosphoric triamide was combined with 100 mg of sodium azide and stirred at 40° C. for 4 hours. The cooled-off reaction mixture was combined with 100 ml of ice water, extracted five times with respectively 50 ml of ether, the organic phase was washed three times with sodium chloride solution, dried over magnesium sulfate, and concentrated under vacuum. The title compound, thus produced as an oil which was uniform as per thin-layer chromatography, was utilized without further purification in the next reaction.

IR: 3400 (broad), 2960, 2920, 2870, 2100, 1735, 1450, 1435, 975 cm$^{-1}$.

4(f)
(5Z,13E)-(8R,9S,11R,12R,15S)-9-Azido-11,15-dihydroxy-19-methyl-5,13,18-prostatrienoic Acid The azide obtained in the preceding reaction stage [Example 4(e)] was introduced into 8.4 ml of a solution of 3.6 g of potassium hydroxide, 24 ml of water, and 120 ml of methanol and stirred under argon at room temperature for 4 hours. The reaction solution was thereafter poured into 40 ml of water and washed once with ether/hexane=1/1; the aqueous phase was then cooled to 5° C., acidified to pH 6 with 10% citric acid solution, and extracted five times with respectively 50 ml of methylene chloride. The combined organic phases were washed with 100 ml of saturated sodium chloride solution, dried over magnesium sulfate, and concentrated under vacuum. The evaporation residue was purified by column chromatography on silica gel with ethyl acetate/0–5% methanol as the mobile phase, thus obtaining 180 mg of the title compound as a colorless oil.

IR: 3400 (broad), 2960, 1920, 1875, 2110, 1710, 1450, 1430, 975 cm$^{-1}$.

EXAMPLE 5

(13E,18Z)-(11R,15S,16RS)-11,15-Dihydroxy-19-chloro-16-methyl-9α,6-nitrilo-13,18-prostadienoic Acid A solution of 190 mg of (5Z,13E,18Z)-(8R,9S,11R,12R,15S,16RS)-9-azido-11,15-dihydroxy-19-chloro-16-methyl-5,13,18-prostatrienoic acid in 18 ml of ethyl acetate was agitated for 26 hours at 80° C. under argon. Then the mixture was evaporated under vacuum to dryness and the residue purified by column chromatography on silica gel with ethyl acetate/5–50% methanol as the mobile phase, thus obtaining 90 mg of the title compound as a colorless oil.

IR (Film): 3400 (broad), 1710, 1665, 1635, 1085, 1020, 970 cm$^{-1}$.

The starting material for the above title compound was prepared as follows:

5(a) 2-[(2Z)-3-Chloro-2-butenyl]-2-methylmalonic Acid Diethyl Ester 11.5 g of sodium cut into small pieces was introduced into a three-necked flask equipped with agitator, reflux condenser, and dropping funnel. To this charge was added dropwise 250 ml of absolute ethanol so quickly that the solution was boiling vigorously. Then 87 g of distilled diethyl methylmalonate was added dropwise to the hot alcoholate solution. After allowing the mixture to cool to about 75° C., the reaction solution was combined with 66 g of 1,3-dichloro-2-butene dropwise; the solution turned yellow during this step. After 2 hours of agitation under heating, the suspension, at this point having pH 5–6 and being almost completely decolorized, was freed of precipitated sodium chloride by filtration. The filtrate was concentrated and combined with the methylene chloride obtained by washing the precipitate. The organic solution was thereafter shaken with saturated sodium chloride solution, dried over magnesium sulfate, concentrated on a forced circulation evaporator, and fractionated under vacuum. Yield: 105 g of the desired diester, bp$_{2.5}$ 110° C.

IR (Film): 1738, 1666, 1160, 1050 cm$^{-1}$.

5(b) 2-[(2Z)-3-Chloro-2-butenyl]-2-methylmalonic Acid 46 g of the diester obtained in the preceding reaction stage was heated together with 33 g of potassium hydroxide in 85 ml of ethanol and 45 ml of water under reflux for 3.5 hours. After evaporation of the solvent under vacuum, the residue was taken up in 45 ml of water and acidified under ice cooling dropwise with concentrated hydrochloric acid to pH 1. Subsequently the aqueous phase was extracted five times with respectively 200 ml of ether. The combined ether extracts were washed with saturated sodium chloride solution, dried over magnesium sulfate and concentrated to dryness under vacuum. The residue was recrystallized from benzene/cyclohexane, thus obtaining 33.5 g of the diacid, mp 99°–101° C.

IR (KBr): 2700, 2650, 2580, 1700, 1663, 1238 cm$^{-1}$.

5(c) (4Z)-5-Chloro-2-methyl-4-hexenoic Acid 33.5 g of the dicarboxylic acid obtained in the preceding reaction stage was heated for 4 hours to 160° C., thus liberating $CO_2$. The product was thereafter distilled under vacuum, thus obtaining 24.3 g of the monocarboxylic acid, bp$_{13}$ 133°–135° C.

IR (Film): 2660, 2570, 1710, 1668, 1243 cm$^{-1}$.

5(d) (4Z)-5-Chloro-2-methyl-4-hexenoic Acid Methyl Ester 153 ml of N-ethyldiisopropylamine and 307 ml of iodomethane were added dropwise in succession to a solution of 24.3 g of the carboxylic acid obtained according to the above description in 450 ml of acetonitrile. After 4 hours of stirring at room temperature, the reaction solution was combined with ice-cold saturated sodium chloride solution and extracted with ethyl acetate. The combined organic phases were washed in succession with sodium bisulfate, sodium bicarbonate, and saturated sodium chloride solution, dried over sodium sulfate, and evaporated on a forced circulation evaporator. The residue was distilled under vacuum, thus isolating 21.9 g of the desired ester, bp$_{13}$ 81°–83° C.

IR (Film): 1738, 1665, 1195, 1172 cm$^{-1}$.

5(e) 2-[(3Z)-4-Chloro-1-methyl-3-pentenyl]-2-oxoethanephosphonic Acid Dimethyl Ester Under argon at −60° C., 247.5 ml of a 2.02-molar butyllithium solution in hexane was added dropwise to a solution of 67.1 g of methanephosphonic acid dimethyl ester in 840 ml of absolute tetrahydrofuran. After 15 minutes, a solution of 44.16 g of the ester obtained according to the above directions in 100 ml of absolute tetrahydrofuran was added dropwise thereto. The reaction mixture was maintained at −65° C. for 3.5 hours, then overnight at −32° C., and finally was allowed to warm up to room temperature. Thereafter it was combined with 28.6 ml of glacial acetic acid and evaporated to dryness under vacuum. The residue was distributed in a two-phase system of 175 ml of water and 825 ml of ether; the organic phase was dried over magnesium sulfate and concentrated on a forced circulation evaporator. The evaporation residue was freed of volatile by-products and unreacted educt by distillation at 40° C./0.1 mm and then purified by column chromatography on silica gel with hexane/50–100% ethyl acetate as the mobile phase. Besides 13.8 g of educt, 36 g of phosphonate was obtained.

IR (Film): 1712, 1666, 1260, 1032 cm$^{-1}$.

5(f)
(1S,5R,6R,7R)-7-Benzoyloxy-6-[(1E,6Z)-(4RS)-7-chloro-4-methyl-3-oxo-1,6-octadienyl]-2-oxabicyclo[3,3,0]octan-3-one Under argon at room temperature, 5.4 g of the phosphonate obtained in the preceding reaction stage (dissolved in 60 ml of absolute dimethoxyethane) was added dropwise to a suspension of 0.96 g of 50% (oil-suspended) sodium hydride in 90 ml of dimethoxyethane freshly distilled over lithium aluminum hydride. After adding 0.9 g of lithium chloride (previously dried under vacuum at 50° C. for 2 hours), the reaction mixture was stirred for 1.5 hours at room temperature. The suspension was then cooled to −20° C. and combined dropwise within one-half hour with a solution of 5.5 g of (1S,5R,6R,7R)-6-formyl-7-benzoyloxy-2-oxabicyclo[3,3,0]octan-3-one [E. J. Corey et al., J. Amer. Chem. Soc. 91: 5675 (1969)] in 150 ml of absolute dimethoxyethane. Thereafter the temperature was allowed to rise within 2 hours to 0° C. under agitation. After control by analytical thin-layer chromatography, 2 ml of glacial acetic acid was added dropwise at −10° C. The mixture was then combined with 250 ml of water, the phases were separated, the aqueous phase was extracted three times with respectively about 200 ml of ether, the organic phases were combined and washed with 4% sodium bicarbonate solution and saturated sodium chloride solution. After drying over magnesium sulfate, the solvent was removed on a forced circulation evaporator. The residue was purified by column chromatography on silica gel with hexane/10–50% ethyl acetate as the mobile phase, thus producing 7.2 g of the desired ketone.

IR (Film): 1775, 1720, 1670, 1630, 1600, 1582, 1275, 715 cm$^{-1}$.

5(g)
(1S,5R,6R,7R)-7-Benzoyloxy-6-[(1E,6Z)-(3S,4RS)-7-chloro-3-hydroxy-4-methyl-1,6-octadienyl]-2-oxabicyclo[3,3,0]octan-3-one 4.1 g of sodium borohydride was added in incremental portions to a solution, cooled to −40° C., of 7.2 g of the ketone obtained in the preceding reaction stage in 250 ml of absolute methanol. After 30 minutes of agitation at this temperature, 8.87 ml of glacial acetic acid was added dropwise—likewise at −40° C.—to the reaction solution. After removing the solvent on a forced circulation evaporator, the residue was combined with a two-phase mixture of 200 ml of water and 300 ml of methylene chloride; the separated aqueous phase was mixed with solid sodium chloride and extracted twice with respectively about 200 ml of methylene chloride. The combined organic phases were washed with saturated sodium chloride solution, dried over magnesium sulfate, and evaporated under vacuum. The isomer separation of the residue took place by column chromatography on silica gel with hexane/10–60% ethyl acetate as the mobile phase. As the least polar product, 3.3 g of the title compound was isolated.

IR (Film): 3480 (broad), 1772, 1715, 1667, 1600, 1580, 1273, 1172, 713 cm$^{-1}$.

5(h)
(1S,5R,6R,7R)-6-[(1E,6Z)-(3S)-(4RS)-7-Chloro-3-hydroxy-4-methyl-1,6-octadienyl]-7-hydroxy-2-oxabicyclo[3,3,0]octan-3-one A solution of 7.1 g of the benzoate obtained in the preceding reaction stage [Example 3(g)] in 335 ml of absolute methanol was combined with 2.4 g of potassium carbonate (anhydrous) and stirred under argon at room temperature for 4 hours. Thereafter 335 ml of 0.1 N hydrochloric acid was added to the reaction mixture and the latter stirred for another 15 minutes. After concentration of the solution, it was extracted with ethyl acetate, the combined organic phases were then washed with saturated sodium chloride solution, dried, and evaporated to dryness. The residue was purified by column chromatography on silica gel with hexane/5–0–100% ethyl acetate as the mobile phase, thus obtaining 4.3 g of the title compound.

IR (Film): 3460, 1770, 1665, 1175, 1035 cm$^{-1}$.

5(i)
(1S,5R,6R,7R)-6-[(1E,6Z)-(3S)-(4RS)-7-Chloro-3-(tetrahydropyran-2-yloxy)-4-methyl-1,6-octadienyl]-7-(tetrahydropyran-2-yloxy)-2-oxabicyclo[3,3,0]octan-3-one 3.6 ml of dihydropyran, freshly distilled over potassium hydroxide, and 0.55 g of pyridine-p-toluenesulfonate were added to a solution of 4.3 g of the diol obtained in the preceding reaction stage in 140 ml of absolute methylene chloride. After 20 hours of stirring at room temperature, the reaction solution was washed with semisaturated sodium chloride solution, dried over magnesium sulfate, and concentrated under vacuum. The evaporation residue was purified by column chromatography on silica gel with ether as the mobile phase, thus producing 6.2 g of the title compound.

IR (Film): 1775, 1665, 1180, 1125, 1080, 1025, 975, 810 cm$^{-1}$.

5(j)
(2RS,3aR,4R,5R,6aS)-4-[(1E,6Z)-(3S)-(4RS)-7-Chloro-3-(tetrahydropyran-2-yloxy)-4-methyl-1,6-octadienyl]-5-(tetrahydropyran-2-yloxy)perhydrocyclopenta[b]furan-2-ol Under argon, 17.6 ml of a 20% diisobutyl aluminum hydride solution in toluene was added dropwise within 10–15 minutes to a solution, cooled to −70° C., of the 6.2 g of lactone obtained in the preceding reaction stage in 170 ml of absolute toluene. The mixture was stirred for another 10 minutes and then 1.3 ml of isopropanol and, at 0° C., 10 ml of water were added thereto, whereafter the mixture was agitated for a further 10 minutes. The resultant white, grainy precipitate was separated by way of a porous filter and washed with ethyl acetate. The organic phases were washed three times with saturated sodium chloride solution, dried over magnesium sulfate, and concentrated under vacuum, thus producing 6.2 g of an oil used without further purification in the subsequent reaction stage.

5(k)
(5Z,13E,18Z)-(8R,9S,11R,12R,15S,16RS)-19-Chloro-9-hydroxy-11,15-bis(tetrahydropyran-2-yloxy)-16-methyl-5,13,18-prostatrienoic Acid A solution of 13.5 g of potassium tert.butylate in 240 ml of absolute dimethyl sulfoxide (heated for 15 minutes to 70° C.) was added dropwise at about 15° C. to a solution of 17 g of 4-carboxybutyltriphenylphosphonium bromide (dried for 1.5 hours at 75°–80° C. on an oil pump) in 70 ml of absolute dimethyl sulfoxide. After 30 minutes of agitation at room temperature, this ylene solution was added dropwise at 15° C. within 15 minutes to a solution of the 6.2 g of lactol obtained in the preceding reaction step in 100 ml of absolute dimethyl sulfoxide. The reaction mixture was then stirred for 5.5 hours at room temperature, then combined with about 300 ml of an ice/water mixture, and extracted three times with ether. The aqueous phase was adjusted to pH 4 with 10% citric acid solution and extracted respectively three times with a 1/1 mixture of ether/hexane and methylene chloride. As per analytical thin-layer chromatography, the methylene chloride phase could be discarded. The other organic phases were combined, washed three times with saturated sodium chloride solution, dried over sodium sulfate, and concentrated on a forced circulation evaporator. The residue was purified by column chromatography on silica gel with hexane/20–100% ethyl acetate as the mobile phase, thus producing 4 g of the desired carboxylic acid.

IR (KBr): 2730, 2650, 1725, 1700, 1660, 1130, 1072, 1018, 970 cm$^{-1}$.

5(l)
(5Z,13E,18Z)-(8R,9S,11R,12R,15S,16RS)-19-Chloro-9-hydroxy-11,15-bis(tetrahydropyran-2-yloxy)-16-methyl-5,13,18-prostatrienoic Acid Methyl Ester 4 g of the carboxylic acid obtained according to the directions set out above was dissolved in a small amount of methylene chloride and combined with ethereal diazomethane solution until the evolution of gas ceased and the reaction mixture assumed a permanent yellow color. After removal of the excess diazomethane as well as the solvent under vacuum at room temperature, 4 g of the title compound was obtained as a colorless oil.

IR (Film): 3400 (broad), 2930, 2870, 1740, 1665, 1135, 1080, 1020, 970 cm$^{-1}$.

5(m)
(5Z,13E,18Z)-(8R,9S,11R,12R,15S,16RS)-19-Chloro-16-methyl-11,15-bis(tetrahydropyran-2-yloxy)-9-tosyloxy-5,13,18-prostatrienoic Acid Methyl Ester A solution of 4 g of the carboxylic acid ester obtained in the preceding reaction stage [Example 5(l)] in 6.7 ml of dry pyridine was combined at 0° C. and under argon with 2.64 g of p-toluenesulfonyl chloride and stirred for 50 hours at room temperature. After adding 3.8 ml of water, the mixture was agitated for another 2 hours at room temperature. Then the reaction solution was diluted with 1 liter of ether, washed in succession with water, twice with respectively 30 ml of ice-cold 5% sulfuric acid, with water, with 30 ml of sodium carbonate solution, and then until neutral with water, dried over magnesium sulfate, and evaporated to dryness under vacuum. The colorless oil was purified by column chromatography on silica gel with hexane/30–50% ethyl acetate as the mobile phase, thus obtaining 4.1 g of the title compound.

IR (Liquid Film): 2940, 2880, 1740, 1660, 1600, 1495, 1370, 1170, 1030, 1020, 975 cm$^{-1}$.

5(n)
(5Z,13E,18Z)-(8R,9R,11R,12R,15S,16RS)-19-Chloro-9-hydroxy-11,15-bis(tetrahydropyran-2-yloxy)-16-methyl-5,13,18-prostatrienoic Acid Methyl Ester The 4.1 g obtained in the preceding reaction stage according to Example 5(m) was dissolved in 85 ml of dimethyl sulfoxide and combined with 8.4 g of potassium nitrite. After 4.5 hours of agitation at 65° C. (during which step the solution first turned green, then brown), the reaction mixture was poured into 400 ml of saturated sodium chloride solution, then extracted five times with respectively 250 ml of ether, the combined organic phases were washed neutral with water, dried over magnesium sulfate, and concentrated under vacuum. The residue was purified by column chromatography on silica gel with ethyl acetate/hexane = 1/1 as the mobile phase, thus obtaining 1.62 g of the desired compound as a colorless oil.

IR (Film): 3400 (broad), 1735, 1665, 1130, 1070, 1020, 970 cm$^{-1}$.

5(o)
(5Z,13E,18Z)-(8R,9R,11R,12R,15S,16RS)-19-Chloro-16-methyl-11,15-bis(tetrahydropyran-2-yloxy)-9(p-toluenesulfonyloxy)-5,13,18-prostatrienoic Acid Methyl Ester At 0° C., 1 g of p-toluenesulfonyl chloride was added to a solution of 1.62 g of the 9β-alcohol produced in the preceding reaction stage in 2.8 ml of dry pyridine. The reaction solution was then stirred under argon for 20 hours at room temperature. After dilution with ether, the reaction mixture was washed successively with water, ice-cold 5% sulfuric acid, water, sodium bicarbonate solution, and again with water, dried over magnesium sulfate, evaporated under vacuum, and the residue purified by column chromatography on silica gel with hexane/30% ethyl acetate as the mobile phase, thus producing 1.64 g of the title compound.

IR (Film): 2960, 2870, 1740, 1660, 1600, 1490, 1370, 1175, 1030, 1020, 975 cm$^{-1}$.

5(p)
(5Z,13E,18Z)-(8R,9R,11R,12R,15S,16RS)-19-Chloro-11,15-dihydroxy-16-methyl-9-(p-toluenesulfonyloxy)-5,13,18-prostatrienoic Acid Methyl Ester Under argon at room temperature, the 1.64 g of 9β-tosylate obtained according to Example 5(o) was agitated for 20 hours with 47 ml of a mixture of acetic acid/water/tetrahydrofuran (65/35/10). The reaction mixture was subsequently combined with 250 ml of saturated sodium chloride solution, extracted three times with respectively 100 ml of ethyl acetate, the organic phase was washed with saturated sodium bicarbonate solution and thereafter neutral with water, dried over sodium sulfate, and evaporated under vacuum. The evaporation residue was subjected to column chromatography on silica gel with ethyl acetate/hexane = 2/1 as the mobile phase, thus obtaining 1.0 g of the tosylate as a colorless oil.

IR (Film): 3400 (broad), 2950, 2920, 2860, 1740, 1665, 1590, 1495, 1360, 1175, 1095, 970 cm$^{-1}$.

5(q)
(5Z,13E,18Z)-(8R,9S,11R,12R,15S,16RS)-9-Azido-19-chloro-11,15-dihydroxy-16-methyl-5,13,18-prostatrienoic Acid Methyl Ester A solution of 1.0 g of the diol produced according to Example 5(p) in 21 ml of hexamethylphosphoric triamide was mixed with 206 mg of sodium azide and agitated for 4.5 hours at 40° C. The cooled-off reaction mixture was combined with 100 ml of ice water, extracted five times with respectively 50 ml of ether, the organic phase was washed three times with sodium chloride solution, dried over magnesium sulfate, and evaporated under vacuum. The title compound obtained in this way as an oil uniform as per thin-layer chromatography was utilized in the subsequent reaction without further purification.

IR (Film): 3400 (broad), 2960, 2930, 2870, 2100, 1735, 1663, 975 cm$^{-1}$.

5(r) (5Z,13E,18Z)-(8R,9S,11R,12R,15S,16RS)-9-Azido-19-chloro-11,15-dihydroxy-16-methyl-5,13,18-prostatrienoic Acid The azide obtained in the preceding reaction stage [Example 5(q)] was introduced into 17.5 ml of a solution of 3.6 g of potassium hydroxide, 24 ml of water, and 120 ml of methanol and stirred under argon at room temperature for 4 hours. The reaction solution was then poured into 40 ml of water and washed once with ether/hexane=1/1; then the aqueous phase was cooled to 5° C., acidified to pH 6 with 10% citric acid solution, and extracted five times with respectively 50 ml of methylene chloride. The combined organic phases were washed with 100 ml of saturated sodium chloride solution, dried over magnesium sulfate, and concentrated under vacuum. The evaporation residue was subjected to purification by column chromatography on silica gel with ethyl acetate/0-5% methanol as the mobile phase, thus obtaining 190 mg of the title compound as a colorless oil.

IR (Film): 3400 (broad), 2950, 2920, 2875, 2110, 1705, 1660, 975 cm$^{-1}$.

EXAMPLE 6

(13E)-(11R,15S)-11,15-Dihydroxy-16-(2-cyclohexenyl)-17,18,19,20-tetranor-9α,6-nitrilo-13-prostenoic Acid A solution of 240 mg of (5Z,13E)-(8R,9S,11R,12R,15S)-9-azido-11,15-dihydroxy-16-(2-cyclohexenyl)-17,18,19,20-tetranor-5,13-prostadienoic acid in 23 ml of ethyl acetate was stirred under argon at 80° C. for 26 hours. The mixture was then concentrated under vacuum and the residue purified by column chromatography on silica gel with ethyl acetate/3-50% methanol as the mobile phase, thus obtaining 110 mg of the title compound as a colorless oil.

IR (Film): 3400 (broad), 2960, 2920, 2865, 1705, 1640, 1080, 1020, 975 cm$^{-1}$.

The starting material for the above title compound was prepared as follows:

6(a) 2-(2-Cyclohexenyl)malonic Acid Diethyl Ester

Within 2 hours, 1.1 l of ethanol was added dropwise to 69 g of finely chopped sodium in a 2-liter three-necked flask equipped with dropping funnel, reflux condenser, and agitator. The hot alcoholate solution was combined dropwise—again within 2 hours—with 196 g of diethyl malonate. After allowing the reaction mixture to cool, 296 g of trans-1,2-dibromocyclohexane was added—within 2 hours—to the reaction solution, which latter was then boiled under reflux overnight. After concentration of the reaction solution on a forced circulation evaporator, the residue was combined with ether and dilute hydrochloric acid, the organic phase then washed with saturated sodium chloride solution, concentrated, and distilled under vacuum, thus obtaining 197 g, bp$_1$ 119°-121° C.

IR (Film): 1750, 1735, 1650 (weak), 1180, 1035 cm$^{-1}$.

6(b) (2-Cyclohexenyl)acetic Acid 100 g of 2-(2-cyclohexenyl)malonic acid diethyl ester and 52 g of potassium hydroxide in 100 ml of water/methanol=¼ was refluxed overnight. Then the alcohol was withdrawn on a forced circulation evaporator, the residue was diluted with about 200 ml of water and then combined under ice cooling with about 70 ml of concentrated hydrochloric acid to pH 1. The mixture was repeatedly extracted with ether, the combined organic phases were washed with saturated sodium chloride solution and evaporated to dryness. The residue was heated for 4 hours to 130° C. with liberation of $CO_2$ and thereafter distilled under vacuum, thus obtaining 55.5 g, bp$_1$ 98°-107° C.

IR (Film): 3030, 2670, 2600, 1715, 1650 (weak) cm$^{-1}$.

6(c) (2-Cyclohexenyl)acetic Acid Methyl Ester

The 55.5 g of carboxylic acid obtained in the preceding reaction stage was reacted with diazomethane and thereafter distilled under vacuum, thus obtaining 46 g, bp$_{0.1}$ 34°-36° C.

IR (Film): 1740, 1650 (weak), 1165 cm$^{-1}$.

6(d) 3-(Cyclohex-2-enyl)-2-oxopropanephosphonic Acid Dimethyl Ester

Under argon at −60° C., 113 ml of a 1.77-molar butyllithium solution in hexane was added dropwise to a solution of 25.6 g of dimethyl methanephosphonate in 300 ml of absolute tetrahydrofuran. After 15 minutes, a solution of 15.4 g of the ester obtained according to the above directions in 50 ml of absolute tetrahydrofuran was added dropwise thereto; the reaction mixture was maintained for 2 hours at −65° C. and then allowed to warm up to room temperature within 2 hours. Thereafter the mixture was combined with 11.4 ml of glacial acetic acid and evaporated to dryness under vacuum. The residue was distributed in a two-phase system of 70 ml of water and 330 ml of ether, the organic phase was dried over magnesium sulfate and concentrated on a forced circulation evaporator. The evaporation residue was freed of volatile by-products and unreacted educt by distillation at 40° C./0.1 mm and then purified by column chromatography on silica gel, mobile phase hexane/10-90% ethyl acetate, thus obtaining 13.65 g of the desired phosphonate.

IR (Film): 1710, 1640 (weak), 1260, 1025 cm$^{-1}$.

6(e) (1S,5R,6R,7R)-7-Benzoyloxy-6-[(E)-3-oxo-4-(2-cyclohexenyl)-1-butenyl]-2-oxabicyclo[3,3,0]octan-3-one Under argon at room temperature, 6.29 g of the phosphonate of Example 6(d) dissolved in 50 ml of dimethoxyethane was added dropwise to a suspension of 1.2 g of 50% sodium hydride (oil suspension) in 100 ml of dimethoxyethane (freshly distilled over lithium aluminum hydride). After adding 1.08 g of dry lithium chloride, the reaction mixture was stirred for 2 hours at room temperature. The suspension was then cooled to −20° C. and combined dropwise with 7 g of "Corey aldehye" [J. Amer. Chem. Soc. 91: 5675 (1969)], dissolved in 160 ml of dimethoxyethane. The temperature was subsequently allowed to rise within 2.5 hours to 0° C., then the mixture was combined dropwise with 2.5 ml of glacial acetic acid at −10° C., 150 ml of water was added, the phases were separated, and the aqueous phase was extracted five times with ether. The combined phases were washed with 4% sodium bicarbonate solution and saturated sodium chloride solution, dried over magnesium sulfate, and concentrated. The residue was purified by column chromatography on silica gel with hexane/5-50% ethyl acetate as the mobile phase, thus obtaining 8.74 g of product, mp 78°-79° C. (ether/hexane).

IR (KBr): 1775, 1720, 1675, 1630, 1600, 1580, 1275, 1180, 720 cm$^{-1}$.

6(f)
(1S,5R,6R,7R,3'S)-7-Benzoyloxy-6-[(E)-3-hydroxy-4-(2-cyclohexenyl)-1-butenyl]-2-oxabicyclo[3,3,0]octan-3-one 5.27 g of sodium borohydride was added in incremental portions under agitation to a solution of 8.74 g of the ketone obtained in the preceding reaction stage [Example 6(e)] in 280 ml of absolute methanol and 120 ml of absolute tetrahydrofuran, which solution was held under argon and cooled to −40° C. After 20 minutes of additional agitation at this temperature, the mixture was combined with 11.5 ml of glacial acetic acid and then concentrated on a forced circulation evaporator. The residue was taken up in about 130 ml of water and 280 ml of methylene chloride. The separated aqueous phase was mixed with solid sodium chloride and extracted twice with respectively about 200 ml of methylene chloride. The combined organic phases were washed with saturated sodium chloride solution, dried over magnesium sulfate, and evaporated under vacuum. The separation of isomers in the residue was accomplished by column chromatography on silica gel with hexane/10-60% ethyl acetate as the mobile phase. 4.65 g of the title compound was isolated as the least polar product.

IR (Film): 3470 (broad), 1770, 1715, 1600, 1580, 1275, 1175, 715 cm$^{-1}$.

6(g)
(1S,5R,6R,7R)-6-[(E)-(3S)-3-Hydroxy-4-(2-cyclohexenyl)-1-butenyl]-7-hydroxy-2-oxabicyclo[3,3,0]octan-3-one A solution of 4.65 g of the benzoate obtained according to Example 6(f) in 230 ml of absolute methanol was combined with 1.6 g of potassium carbonate (anhydrous) and stirred under argon at room temperature for 4 hours. Subsequently, 230 ml of 0.1 N hydrochloric acid was added to the reaction mixture and the latter stirred for another 15 minutes. After evaporation of the solution, the latter was extracted with ethyl acetate, the combined organic phases then washed with saturated sodium chloride solution, dried, and concentrated under vacuum. Yield: 3.2 g of the desired diol. A chromatographic purifying step was unnecessary.

IR (Film): 3460 (broad), 1770, 1635, 1180 cm$^{-1}$.

6(h)
(1S,5R,6R,7R)-6-[(E)-(3S)-3-(Tetrahydropyran-2-yloxy)-4-(2-cyclohexenyl)-1-butenyl]-7-(tetrahydropyran-2-yloxy)-2-oxabicyclo[3,3,0]octan-3-one 2.9 ml of dihydropyran, freshly distilled over potassium hydroxide, and 450 mg of pyridine-p-toluenesulfonate were added to a solution of 3.2 g of the diol obtained in the preceding reaction stage in 120 ml of absolute methylene chloride. After 19 hours of agitation at room temperature, the reaction solution was washed with semisaturated sodium chloride solution, dried over magnesium sulfate, and concentrated under vacuum. The evaporation residue was purified by column chromatography on silica gel with ether as the mobile phase, thus obtaining 4.6 g of the title compound.

IR (KBr): 1770, 1760, 1175, 1130, 1075, 1025, 975, 810 cm$^{-1}$.

6(i)
(2RS,3aR,4R,5R,6aS)-4-[(E)-(3S-3-(Tetrahydropyran-2-yloxy)-4-(2-cyclohexenyl)-1-butenyl]-5-(tetrahydropyran-2-yloxy)perhydrocyclopenta[b]furan-2-ol Within 10–15 minutes, 13.7 ml of a 20% diisobutyl aluminum hydride solution in toluene was added dropwise to a solution, cooled to −70° C., of the 4.6 g of lactone obtained in the preceding reaction stage [Example 6(h)] in 150 ml of absolute toluene under argon. The mixture was stirred for another 5 minutes, then 1 ml of isopropanol was added dropwise thereto, and at 0° C. 16 ml of water was furthermore introduced into the reaction mixture, whereafter it was stirred for another 10 minutes. The resultant white, grainy precipitate was separated via a porous filter plate and washed with ethyl acetate. The organic phases were washed three times with saturated sodium chloride solution, dried over magnesium sulfate, and concentrated under vaccum, thus obtaining 4.6 g of an oil used without further purification in the subsequent reaction stage.

6(j)
(5Z,13E)-(8R,9S,11R,12R,15S)-9-Hydroxy-11,15-bis(-tetrahydrofuran-2-yloxy)-16-(2-cyclohexenyl)-17,18,19,20-tetranor-5,13-prostadienoic Acid At about 15° C., 96 ml of a solution of methanesulfinylmethyl sodium in absolute dimethyl sulfoxide (solution: 7.5 g of 50% sodium hydride suspension in 150 ml of absolute dimethyl sulfoxide was stirred for one-half hour at 70° C.) was added dropwise to a solution of 22 g of 4-carboxybutyltriphenylphosphonium bromide (dried for 1.5 hours at 75°–80° C. on an oil pump) in 90 ml of absolute dimethyl sulfoxide. After 30 minutes of agitation at room temperature, this ylene solution was added dropwise at 15° C. within 15 minutes to a solution of the 4.6 g of lactol obtained in the preceding reaction step [Example 6(i)] in 90 ml of absolute dimethyl sulfoxide. The reaction mixture was then stirred for 3 hours at room temperature, then mixed with 200 ml of ice/water mixture, and extracted three times with ether. The aqueous phase was adjusted to pH 4 with 10% citric acid solution and extracted respectively three times with a 1/1 mixture of ether/hexane and methylene chloride. As per analytical thin-layer chromatography, the ether and methylene chloride phases could be discarded. The ether/hexane phase was washed three times with saturated sodium chloride solution, dried over magnesium sulfate, and concentrated on a forced circulation evaporator. The residue was purified by column chromatography on silica gel with hexane/5-0–80% ethyl acetate as the mobile phase, thus obtaining 3.6 g of the carboxylic acid as the title compound.

IR (Film): 3460 (broad), 2740, 2660, 1735, 1710, 1135, 1080, 1020, 975, 810 cm$^{-1}$.

6(k)
(5Z,13E)-(8R,9S,11R,12R,15S)-9-Hydroxy-11,15-bis(-tetrahydropyran-2-yloxy)-16-(2-cyclohexenyl)-17,18,19,20-tetranor-5,13-prostadienoic Acid Methyl Ester The 3.6 g of carboxylic acid obtained in the preceding reaction step was dissolved in a small amount of methylene chloride and combined with ethereal diazomethane solution until no gas was liberated any more and the reaction solution assumed a permanent yellow coloring. After removal of the excess diazomethane as well as the solvent under vacuum at room temperature, 3.6 g of the desired methyl ester was obtained as a colorless oil.

IR (Film): 3400 (broad), 1740, 1135, 1075, 1020, 975, 810 cm$^{-1}$.

6(l)
(5Z,13E)-(8R,9S,11R,12R,15S)-11,15-Bis(tetrahydropyran-2-yloxy)-9-tosyloxy-16-(2-cyclohexenyl)-17,18,19,20-tetranor-5,13-prostadienoic Acid Methyl Ester A solution of 3.6 g of the carboxylic acid ester obtained according to Example 6(k) in 6.3 ml of dry pyridine was combined at 0° C. under argon with 2.5 g of p-toluenesulfonyl chloride and stirred for 48 hours at room temperature. After the addition of 3.5 ml of water, the mixture was stirred for another 2 hours at room temperature. Subsequently the reaction solution was diluted with 600 ml of ether, washed in succession with 20 ml of water, twice with respectively 30 ml of ice-cold 5% sulfuric acid, with 20 ml of water, with 30 ml of sodium bicarbonate solution and then until neutral with water, dried over magnesium sulfate, and evaporated to dryness under vacuum. The colorless oil was purified by column chromatography on silica gel with hexane/30–50% ethyl acetate as the mobile phase, thus obtaining 3.76 g of the title compound.

IR (Film): 2940, 2860, 1740, 1600, 1490, 1370, 1175, 1030, 1020, 975 cm$^{-1}$.

6(m)
(5Z,13E)-(8R,9R,11R,12R,15S)-9-Hydroxy-11,15-bis(tetrahydropyran-2-yloxy)-16-(2-cyclohexenyl)-17,18,19,20-tetranor-5,13-prostadienoic Acid Methyl Ester The 3.76 g obtained in the preceding reaction stage according to Example 6(l) was dissolved in 80 ml of dimethyl sulfoxide and combined with 8 g of potassium nitrite. After 5 hours of agitation at 65° C. (during which step the solution first turned green, then brown), the reaction mixture was poured into 300 ml of saturated sodium chloride solution, then extracted five times with respectively 250 ml of ether, the combined organic phases were washed neutral with water, dried over magnesium sulfate, and concentrated to dryness under vacuum. The residue was purified by column chromatography on silica gel with ethyl acetate/hexane = 1/1 as the mobile phase, thus obtaining 1.42 g of the desired compound as a colorless oil.

IR: 3400, 2950, 2870, 1740, 1030, 1020, 975 cm$^{-1}$.

6(n)
(5Z,13E)-(8R,9R,11R,12R,15S)-11,15-Bis-(tetrahydropyran-2-yloxy)-9-(p-toluenesulfonyloxy)-16-(2-cyclohexenyl)-17,18,19,20-tetranor-5,13-prostadienoic Acid Methyl Ester At 0° C., 675 mg of p-toluenesulfonyl chloride was added to a solution of 1.4 g of the 9β-alcohol prepared in the preceding reaction stage in 1.7 ml of dry pyridine. The reaction solution was then stirred under argon at room temperature for 20 hours. After dilution with ether, the reaction mixture was washed in succession with water, ice-cold 5% sulfuric acid, water, sodium bicarbonate solution and once again water, dried over magnesium sulfate, evaporated under vacuum, and the residue purified by column chromatography on silica gel with hexane/30% ethyl acetate as the mobile phase, thus producing 1.27 g of the title compound.

IR: 2960, 2870, 1740, 1600, 1490, 1370, 1170, 1030, 1020, 975 cm$^{-1}$.

6(o)
(5Z,13E)-(8R,9R,11R,12R,15S)-11,15-Dihydroxy-9-(p-toluenesulfonyloxy)-16-(2-cyclohexenyl)-17,18,19,20-tetranor-5,13-prostadienoic Acid Methyl Ester Under argon, the 1.25 g of 9β-tosylate obtained according to Example 6(n) was stirred at room temperature for 20 hours with 37 ml of a mixture of acetic acid/water/tetrahydrofuran (65/35/10). The reaction mixture was subsequently combined with 150 ml of saturated sodium chloride solution, extracted three times with respectively 100 ml of ethyl acetate, the organic phase was washed with saturated sodium bicarbonate solution and then neutral with water, dried over sodium sulfate, and concentrated under vacuum. The evaporation residue was subjected to column chromatography on silica gel with ethyl acetate/hexane = 2/1 as the mobile phase, thus obtaining 746 mg of the tosylate as a colorless oil.

IR (Film): 3400 (broad), 2950, 2920, 2860, 1735, 1595, 1490, 1360, 1175, 1095, 975 cm$^{-1}$.

6(p)
(5Z,13E)-(8R,9S,11R,12R,15S)-9-Azido-11,15-dihydroxy-16-(2-cyclohexenyl)-17,18,19,20-tetranor-5,13-prostadienoic Acid Methyl Ester A solution of 720 mg of the diol prepared according to Example 6(o) in 16 ml of hexamethylphosphoric triamide was combined with 155 mg of sodium azide and stirred at 40° C. for 4.5 hours. The cooled reaction mixture was combined with 100 ml of ice water, extracted five times with respectively 50 ml of ether, the organic phase was washed three times with sodium chloride solution, dried over magnesium sulfate, and concentrated under vacuum. The title compound, obtained in this way as an oil uniform as per thin-layer chromatography, was utilized in the subsequent reaction without further purification.

IR: 3400 (broad), 2960, 2930, 2870, 2100, 1735, 975 cm$^{-1}$.

6(q)
(5Z,13E)-(8R,9S,11R,12R,15S)-9-Azido-11,15-dihydroxy-16-(2-cyclohexenyl)-17,18,19,20-tetranor-5,13-prostadienoic Acid The azide obtained in the preceding reaction stage [Example 6(p)] was introduced into 13.2 ml of a solution of 3.6 g of potassium hydroxide, 24 ml of water, and 120 ml of methanol and stirred under argon at room temperature for 4 hours. The reaction solution was then poured into 40 ml of water and washed once with ether/hexane = 1/1, whereafter the aqueous phase was cooled to 5° C., acidified with 10% citric acid solution to pH 6, and extracted five times with respectively 50 ml of methylene chloride. The combined organic phases were washed with 100 ml of saturated sodium chloride solution, dried over magnesium sulfate, and evaporated under vacuum. The evaporation residue was purified by column chromatography on silica gel with ethyl acetate/0–5% methanol as the mobile phase, thus producing 255 mg of the title compound as a colorless oil.

IR (Film): 3400 (broad), 2950, 2920, 2875, 2120, 1705, 975 cm$^{-1}$.

EXAMPLE 7

(13E)-(11R,15S,16RS)-11,15-Dihydroxy-16-methyl-16-(2-cyclopenten-1-yl)-17,18,19,20-tetranor-9α,6-nitrilo-13-prostenoic Acid A solution of 260 mg of (5Z,13E)-(8R,9S,11R,12R,15S,16RS)-9-azido-11,15-dihydroxy-16-methyl-16-(2-cyclopenten-1-yl)-17,18,19,20-tetranor-5,13-prostadienoic acid in 25 ml of ethyl acetate was stirred under argon at 80° C. for 27 hours. The mixture was then concentrated under vacuum and the residue purified by column chromatography on silica gel with ethyl acetate/5–50% methanol as the mobile phase, thus obtaining 120 mg of the title compound as a colorless oil.

IR (Film): 3240 (broad), 2960, 2920, 2860, 1710, 1640, 1080, 970 cm$^{-1}$.

The starting material for the above title compound was prepared as follows:

7(a) 2-(2-Cyclopenten-1-yl)-2-methylmalonic Acid Diethyl Ester 52.4 g of sodium, cut into small pieces, was introduced into a three-necked flask equipped with dropping funnel, reflux condenser, and KPG agitator. Under an argon atmosphere, 790 ml of absolute ethanol was added dropwise thereto within 3 hours so that the reaction mixture was boiling vigorously. Within 1.5 hours, 157 g of diethyl methylmalonate was added dropwise to the hot, slightly turbid alcoholate solution. The mixture was agitated for another hour and then 205 g of trans-1,2-dibromocyclopentane was added dropwise within one hour to the cooled-off solution. Thereafter the solution was refluxed for 17 hours. After concentration of the reaction solution on a forced circulation evaporator, the residue was combined with ether and dilute hydrochloric acid, the organic phase was washed neutral with saturated sodium chloride solution, dried over sodium sulfate, and distilled under vacuum, thus obtaining 170 g, bp$_{1.5}$ 90°–105° C.

IR (Film): 1731, 1250, 100 cm$^{-1}$.

7(b) 2-(2-Cyclopenten-1-yl)-2-methylmalonic Acid 156 g of the diester obtained in the preceding reaction stage was heated under reflux together with 83 g of sodium hydroxide in 680 ml of water for 5.5 hours. Thereafter the mixture was concentrated on a forced circulation evaporator and combined dropwise under ice cooling with concentrated hydrochloric acid to pH 1. The precipitate was collected, washed with water, and dissolved in ether. The ether phase was washed with saturated sodium chloride solution, dried over magnesium sulfate, and concentrated under vacuum. The residue was crystallized from ether/toluene, thus obtaining 112 g, mp 153° C.

IR (KBr): 2630, 2530, 1715, 1275 cm$^{-1}$.

7(c) 2-(2-Cyclopenten-1-yl)propionic Acid

The 112 g obtained in the preceding reaction stage was heated for one hour to 176° C. under liberation of carbon dioxide. The product was then distilled under vacuum, thus obtaining 84.4 g of the title compound, bp$_{0.7}$ 81°–83° C.

IR (KBr): 2650, 2520, 1715, 1270 cm$^{-1}$.

7(d) 2-(2-Cyclopenten-1-yl)propionic Acid Methyl Ester

The 84 g of carboxylic acid obtained according to the above directions was combined with such a quantity of ethereal diazomethane solution that there was no longer any evolution of nitrogen upon adding the reagent and the solution assumed a permanent yellow color. The solvent was then removed together with excess diazomethane under vacuum at room temperature, and the residue was fractionated, thus producing 87 g of the ester, bp$_{0.8}$ 43°–44° C.

IR (Film): 1740, 1620 (weak), 1160 cm$^{-1}$.

7(e) [3-(2-Cyclopenten-1-yl)-2-oxobutane]-phosphonic Acid Dimethyl Ester

Under argon at −60° C., 382 ml of a 1.31-molar butyllithium solution in hexane was added dropwise to a solution of 62 g of methanephosphonic acid dimethyl ester in 800 ml of absolute tetrahydrofuran. After one-half hour, a solution of 30.84 g of the carboxylic acid ester obtained in the preceding reaction stage in 75 ml of absolute tetrahydrofuran was added dropwise thereto at the same temperature. The reaction mixture was maintained for 3 hours at −60° C. and then allowed to warm up to room temperature. Then the mixture was combined with 28.6 ml of glacial acetic acid and concentrated on a forced circulation evaporator. The residue was distributed in a two-phase system of ether/water, and the aqueous phase was extracted repeatedly with ether. The combined organic phases were washed with saturated sodium chloride solution, dried over sodium sulfate, and concentrated under vacuum. The residue was chromatographed on a silica gel column with hexane/50–100% ethyl acetate, was well as ethyl acetate/0–7% methanol as the mobile phases, thus obtaining 35.6 g of the desired phosphonate.

IR (Film): 1710, 1258, 1033 cm$^{-1}$.

7(f) (1S,5R,6R,7R)-7-Benzoyloxy-6-[(E)-(4RS)-4-methyl-3-oxo-4-(2-cyclopenten-1-yl)-1-butenyl]-2-oxabicyclo[3,3,0]octan-3-one Under argon at room temperature, 8.0 g of the phosphonate obtained in the preceding reaction stage (dissolved in 85 ml of absolute dimethoxyethane) was added dropwise to a suspension of 1.56 g of 50% (oil-suspended) sodium hydride in 170 ml of dimethoxyethane freshly distilled over lithium aluminum hydride. After adding 1.38 g of lithium chloride (previously dried under vacuum at 50° C. for 2 hours), the reaction mixture was stirred at room temperature for 2 hours. Subsequently the suspension was cooled to −20° C. and combined dropwise within one-half hour with a solution of 8.9 g of (1S,5R,6R,7R)-6-formyl-7-benzoyloxy-2-oxabicyclo[3,3,0]octan-3-one [E. J. Corey et al., J. Amer. Chem. Soc. 91: 5675 (1969)] in 255 ml of absolute dimethoxyethane. The temperature was then allowed to rise within 4.5 hours to −5° C. under agitation. After control executed by analytical thin-layer chromatography, 3.3 ml of glacial acetic acid was then added dropwise to the reaction mixture at −10° C. The mixture was then combined with 450 ml of water, the phases were separated, the aqueous phase was extracted three times with respectively about 200 ml of ether, the organic phases were combined and washed with 4% sodium bicarbonate solution and saturated sodium chloride solution. After drying over magnesium sulfate, the solvent was removed on a forced circulation evaporator. Purification of the residue by column chromatography on silica gel with hexane/50-100% ethyl acetate as the mobile phase yielded 11.85 g of the title compound, mp 85°-87.5° C.

IR (KBr): 1766, 1713, 1688, 1622, 1602, 1582, 1274, 1160, 711 cm$^{-1}$.

7(g)
(1S,5R,6R,7R)-7-Benzoyloxy-6-[(E)-(3S,4RS)-3-hydroxy-4-methyl-4-(2-cyclopenten-1-yl)-1-butenyl]-2-oxabicyclo-[3,3,0]octan-3-one 7.18 g of sodium borohydride was added in incremental portions to a solution, cooled to −40° C., of 11.85 g of the ketone obtained in the preceding reaction stage in 350 ml of absolute methanol. After 75 minutes of additional agitation at this temperature, 15.4 ml of glacial acetic acid was added dropwise to the reaction solution—likewise at −40° C. After removal of the solvent on a forced circulation evaporator, the residue was combined with a two-phase mixture of 200 ml of water and 300 ml of methylene chloride; the separated aqueous phase was combined with solid sodium chloride and extracted twice with respectively about 200 ml of methylene chloride. The combined organic phases were washed with saturated sodium chloride solution, dried over magnesium sulfate, and concentrated under vacuum. The isomer separation of the residue was carried out by column chromatography on silica gel with hexane/50-100% ethyl acetate as the mobile phase, thus isolating 5.7 g of the title compound as the least polar product.

IR (Film): 3490, 1770, 1718, 1602, 1584, 1275, 1178, 713 cm$^{-1}$.

7(h)
(1S,5R,6R,7R)-6-[(E)-(3S,4RS)-3-Hydroxy-4-methyl-4-(2-cyclopenten-1-yl)-1-butenyl]-7-hydroxy-2-oxabicyclo[3,3,0]octan-3-one A solution of 8 g of the benzoate obtained in the preceding reaction stage in 396 ml of absolute methanol was mixed with 2.8 g of anhydrous potassium carbonate and stirred for 3 hours at room temperature and under argon. Then 396 ml of 0.1 N hydrochloric acid was added to the reaction solution and the latter stirred for another 15 minutes. The solution was concentrated and extracted with ethyl acetate; the combined organic phases were washed with saturated sodium chloride solution, dried, and evaporated under vacuum. The residue was purified by column chromatography on silica gel with hexane/80-100% ethyl acetate as the mobile phase, thus producing 4.63 g of the title compound.

IR (Film): 3420 (broad), 1762, 1670 (weak), 1174 cm$^{-1}$.

7(i)
(1S,5R,6R,7R)-6-[(E)-(3S,4RS)-3-(Tetrahydropyran-2-yloxy)-4-methyl-4-(2-cyclopenten-1-yl)-1-butenyl]-7-(tetrahydropyran-2-yloxy)-2-oxabicyclo[3,3,0]octan-3-one At 0° C., 1.64 ml of dihydropyran, freshly distilled over potassium hydroxide, and 33 mg of p-toluenesulfonic acid were added to a solution of 3.54 g of the diol obtained in the preceding reaction stage in 190 ml of absolute methylene chloride. After 3 hours of agitation the reaction solution was washed with saturated sodium bicarbonate solution and water, dried over sodium sulfate, and evaporated under vacuum. The residue was purified by column chromatography on silica gel with hexane/50-100% ethyl acetate as the mobile phase, thus isolating 5.3 g of the di-THP ether.

IR (Film): 1770, 1175, 1130, 1075, 1020, 970, 810 cm$^{-1}$.

7(j)
(2RS,3aR,4R,5R,6aS)-4-[(E)-(3S)-(4RS)-3-(Tetrahydropyran-2-yloxy)-4-methyl-4-(2-cyclopenten-1-yl)-1-butenyl]-5-(tetrahydropyran-2-yloxy)perhydrocyclopenta[b]-furan-2-ol Under argon, 15.7 ml of a 20% diisobutyl aluminum hydride solution in toluene was added dropwise within 10-15 minutes to a solution, cooled to −70° C., of the 5.3 g of lactone obtained in the preceding reaction stage [Example 7(i)] in 150 ml of absolute toluene. The mixture was stirred for 5 minutes, then 1 ml of isopropanol was added dropwise thereto and, at 0° C., 16 ml of water was furthermore added. The mixture was agitated for another 10 minutes. The resultant white, grainy precipitate was separated by way of a porous filter and washed with ethyl acetate. The organic phases were washed three times with saturated sodium chloride solution, dried over magnesium sulfate, and concentrated under vacuum, thus obtained 5.3 g of an oil used without further purification in the subsequent reaction stage.

7(k)
(5Z,13E)-(8R,9S,11R,12R,15S,16RS)-9-Hydroxy-11,15-bis(tetrahydropyran-2-yloxy)-16-methyl-16-(2-cyclopenten-1-yl)-17,18,19,20-tetranor-5,13-prostadienoic Acid 111 ml of a solution of methanesulfinylmethyl sodium in absolute dimethyl sulfoxide (solution: 7.5 g of 50% sodium hydride suspension in 150 ml of absolute dimethyl sulfoxide was agitated for one-half hour at 70° C.) was added dropwise at about 15° C. to a solution of 25 g of 4-carboxybutyltriphenylphosphonium bromide (dried for 1.5 hours at 75°-80° C. on an oil pump) in 90 ml of absolute dimethyl sulfoxide. After 30 minutes of agitation at room temperature, this ylene solution was added dropwise at 15° C. within 15 minutes to a solution of the 5.3 g of lactol obtained in the preceding reaction step [Example 7(j)] in 90 ml of absolute dimethyl sulfoxide. The reaction mixture was then stirred for 3 hours at room temperature, thereafter combined with 200 ml of an ice/water mixture, and extracted three times with ether. The aqueous phase was adjusted to pH 4 with 10% citric acid solution and extracted respectively three times with a 1/1 mixture of ether/hexane and methylene chloride. As per analytical thin-layer chromatography, the ether and methylene chloride phases could be discarded. The ether/hexane phase was washed three times with saturated sodium chloride solution, dried over magnesium sulfate, and evaporated on a forced circulation evaporator. The residue was purified by column chromatography on silica gel with hexane/50-80% ethyl acetate as the mobile phase, thus obtaining 4.3 g of the carboxylic acid as the title compound.

IR (Film): 3460 (broad), 2740, 2660, 1730, 1710, 1120, 1077, 1025, 975 cm$^{-1}$.

7(l)
(5Z,13E)-(8R,9S,11R,12R,15S,16RS)-9-Hydroxy-11,15-bis(tetrahydropyran-2-yloxy)-16-methyl-16-(2-cyclopenten-1-yl)-17,18,19,20-tetranor-5,13-prostadienoic Acid Methyl Ester The 4.3 g of carboxylic acid obtained in the preceding reaction stage was dissolved in a small amount of methylene chloride and combined with such a quantity of ethereal diazomethane solution that no gas was formed any longer and the reaction solution assumed a permanent yellow color. After removal of the excess diazomethane as well as the solvent under vacuum at room temperature, 4.3 g of the desired methyl ester was obtained as a colorless oil.

IR (Film): 3470 (broad), 1740, 1130, 1080, 1020, 975 cm$^{-1}$.

7(m)
(5Z,13E)-(8R,9S,11R,12R,15S,16RS)-11,15-Bis(tetrahydropyran-2-yloxy)-9-tosyloxy-b 16-methyl-16-(2-cyclopenten-1-yl)-17,18,19,20-tetranor-5,13-prostadienoic Acid Methyl Ester A solution of 4.3 g of the carboxylic acid ester obtained according to Example 7(l) in 7.5 ml of dry pyridine was combined at 0° C. under argon with 3 g of p-toluenesulfonyl chloride and stirred for 48 hours at room temperature. After the addition of 4 ml of water, the mixture was stirred for another 2 hours at room temperature. Thereafter the reaction solution was diluted with 600 ml of ether, washed in succession with 20 ml of water, twice with 30 ml each of ice-cold 5% sulfuric acid, 20 ml of water, 30 ml of sodium bicarbonate solution, and then neutral with water, dried over magnesium sulfate, and evaporated to dryness under vacuum. The colorless oil was purified by column chromatography on silica gel with hexane/30-50% ethyl acetate as the mobile phase, thus obtaining 4.4 g of the title compound.

IR (Film): 1740, 1600, 1495, 1370, 1180, 1130, 1080, 1020, 975 cm$^{-1}$.

7(n)
(5Z,13E)-(8R,9R,11R,12R,15S,16RS)-9-Hydroxy-11,15-bis(tetrahydropyran)-2-yloxy)-16-methyl-16-(2-cyclopenten-1-yl)-17,18,19,20-tetranor-5,13-prostadienoic Acid Methyl Ester The 4.4 g obtained in the preceding reaction stage according to Example 7(m) was dissolved in 80 ml of dimethyl sulfoxide and combined with 9.5 g of potassium nitrite. After 6 hours of agitation at 65° C. (during which step the solution turned first green, then brown), the reaction mixture was poured into 300 ml of saturated sodium chloride solution, extracted five times with respectively 250 ml of ether, the combined organic phases were washed neutral with water, dried over magnesium sulfate, and concentrated to dryness under vacuum. The residue was purified by column chromatography on silica gel with ethyl acetate/hexane=1/1 as the mobile phase, thus producing 1.7 g of the desired compound as a colorless oil.

IR: 3400, 2950, 2860, 1740, 1130, 1080, 1020, 970 cm$^{-1}$.

7(o)
(5Z,13E)-(8R,9R,11R,12R,15S,16RS)-11,15-Bis(tetrahydropyran-2-yloxy)-9-(p-toluenesulfonyloxy)-16-methyl-16-(2-cyclopenten-1-yl)-17,18,19,20-tetranor-5,13-prostadienoic Acid Methyl Ester At 0° C., 820 mg of p-toluenesulfonyl chloride was added to a solution of 1.7 g of the 9β-alcohol prepared in the preceding reaction stage in 2 ml of dry pyridine. The reaction solution was then stirred under argon at room temperature for 20 hours. After dilution with ether, the reaction mixture was washed in succession with water, ice-cold 5% sulfuric acid, water, sodium bicarbonate solution and once again with water, dried over magnesium sulfate, evaporated under vacuum, and the residue purified by column chromatography on silica gel with hexane/30% ethyl acetate as the mobile phase, thus obtaining 1.54 g of the title compound.

IR: 2960, 2870, 1735, 1600, 1490, 1370, 1175, 1130, 1020, 975 cm$^{-1}$.

7(p)
(5Z,13E)-(8R,9R,11R,12R,15S,16RS)-11,15-Dihydroxy-9-(p-toluenesulfonyloxy)-16-methyl-16-(2-cyclopenten-1-yl)-17,18,19,20-tetranor-5,13-prostadienoic Acid Methyl Ester The 1.5 g of 9β-tosylate obtained according to Example 7(o) was stirred for 20 hours under argon at room temperature with 45 ml of a mixture of acetic acid/water/tetrahydrofuran (65/35/10). Then the reaction mixture was combined with 150 ml of saturated sodium chloride solution, extracted three times with respectively 100 ml of ethyl acetate, the organic phase was washed with saturated sodium bicarbonate solution and then neutral with water, dried over sodium sulfate, and concentrated under vacuum. The evaporation residue was subjected to column chromatography on silica gel with ethyl acetate/hexane=2/1 as the mobile phase, thus obtaining 900 mg of the tosylate as a colorless oil.

IR (Film): 3400 (broad), 2950, 2920, 2860, 1735, 1595, 1490, 1360, 1175, 1090, 975 cm$^{-1}$.

7(q)
(5Z,13E)-(8R,9S,11R,12R,15S,16RS)-9-Azido-11,15-dihydroxy-16-methyl-16-(2-cyclopenten-1-yl)-17,18,19,20-tetranor-5,13-prostadienoic Acid Methyl Ester A solution of 850 mg of the diol produced according to Example 7(p) in 19 ml of hexamethylphosphoric triamide was combined with 185 mg of sodium azide and stirred for 4 hours at 40° C. The cooled reaction mixture was combined with 100 ml of ice water, extracted five times with respectively 50 ml of ether, the organic phase was washed three times with sodium chloride solution, dried over magnesium sulfate, and evaporated under vacuum. The title compound, thus produced as an oil uniform as per thin-layer chromatography, was used without further purification in the subsequent reaction.

IR: 3400 (broad), 2960, 2930, 2870, 2100, 1735, 970 cm$^{-1}$.

7(r)
(5Z,13E)-(8R,9S,11R,12R,15S,16RS)-9-Azido-11,15-dihydroxy-16-methyl-16-(2-cyclopenten-1-yl)-17,18,19,20-tetranor-5,13-prostadienoic Acid The azide obtained in the preceding reaction stage [Example 7(q)] was introduced into 16 ml of a solution of 3.6 g of potassium hydroxide, 24 ml of water, and 120 ml of methanol and stirred for 4 hours under argon at room temperature. The reaction solution was subsequently poured into 40 ml of water and washed once with ether/hexane=1/1; the aqueous phase was then cooled to 5° C., acidified to pH 6 with 10% citric acid solution, and extracted five times with respectively 50 ml of methylene chloride. The combined organic phases were washed with 100 ml of saturated sodium chloride solution, dried over magnesium sulfate, and concentrated under vacuum. The residue from the evaporation was purified by column chromatography on silica gel with ethyl acetate/0–5% methanol as the mobile phase, thus obtaining 290 mg of the title compound as a colorless oil.

IR (Film): 3420 (broad), 2950, 2920, 2875, 2120, 1705, 970 cm$^{-1}$.

EXAMPLE 8

(13E)-(11R,15S,16RS)-11,15-Dihydroxy-16,19-dimethyl-9α,6-nitrilo-13,18-prostadienoic Acid Methyl Ester A solution of 100 mg of (13E)-(11R,15S,16RS)-11,15-dihydroxy-16,19-dimethyl-9α,6-nitrilo-13,18-prostadienoic acid (Example 1) in a small amount of methylene chloride was combined at −10° C. with such an amount of ethereal diazomethane solution that there was no longer any liberation of gas, and the solution assumed a permanent yellow coloring. After removal of the excess diazomethane under vacuum at room temperature, 80 mg of the title compound was obtained as a colorless oil.

IR (Film): 3450 (broad), 2960, 2860, 1735, 975 cm$^{-1}$.

EXAMPLE 9

Tris(hydroxymethyl)aminomethane Salt of (13E)-(11R,15S,16RS)-11,15-Dihydroxy-16,19-dimethyl-9α,6-nitrilo-13,18-prostadienoic Acid At 65° C., a solution of 34 mg of tris(hydroxymethyl)aminomethane in 0.2 ml of water was added to a solution of 100 mg of (13E)-(11R,15S,16RS)-11,15-dihydroxy-16,19-dimethyl-9α,6-nitrilo-13,18-prostadienoic acid (Example 1) in 20 ml of acetonitrile. The mixture was cooled under agitation, decanted after 14 hours, and the residue dried at 25° C./0.1 torr, thus obtaining 85 mg of the title compound.

EXAMPLE 10

(13E)-(11R,15S,16RS)-11,15-Dihydroxy-16,19-dimethyl-9α,6-nitrilo-13,18-prostadienoic Acid Butyl Ester Analogously to Example 8, the title compound was obtained as a colorless oil from the acid prepared according to Example 1 with diazobutane.

IR (Film): 3430 (broad), 2960, 2920, 2860, 1740, 970 cm$^{-1}$.

EXAMPLE 11

(13E)-(11R,15S,16RS)-11,15-Dihydroxy-16,20-dimethyl-9α,6-nitrilo-13-prosten-18-ynoic Acid A solution of 250 mg of (5Z,13E)-(9S,11R,15S,16RS)-9-azido-11,15-dihydroxy-16,20-dimethyl-5,13-prostadien-18-ynoic acid in 20 ml of ethyl acetate was heated under argon for 22 hours to 70°–75° C. After evaporation of the solvent under vacuum, the residue was purified on silica gel with methylene chloride/10–30% isopropanol as the mobile phase, thus obtaining 176 mg of the title compound as a colorless oil.

IR (Film): 3610, 3380 (broad), 2960, 2850, 1715, 1640, 1020, 975 cm$^{-1}$.

The starting material for the above title compound was produced as follows:

11(a)

(1S,5R,6R,7R)-7-Benzoyloxy-6-[(E)-(4RS)-4-methyl-3-oxonon-1-en-6-inyl]-2-oxabicyclo[3,3,0]octan-3-one Analogously to Example 1(g), 14.2 g of the title compound was synthesized from 9.85 g of 3-methyl-2-oxooct-5-inylphosphonic acid dimethyl ester and 11 g of (1S,5R,6R,7R)-6-formyl-7-benzoyloxy-2-oxabicyclo[3,3,0]octan-3-one [E. J. Corey et al., J. Amer. Chem. Soc. 91: 5675 (1969)].

IR (Film): 1775, 1715, 1685, 1670, 1620, 1600, 1578, 1272, 1182, 715 cm$^{-1}$.

11(b)

(1S,5R,6R,7R)-7-Benzoyloxy-6-[(E)-(3S,4RS)-3-hydroxy-4-methylnon-1-en-6-inyl]-2-oxabicyclo[3,3,0]octan-3-one Analogously to the directions in Example 1(h), the 14.2 g of ketone obtained in the preceding reaction stage was reacted with sodium borohydride, thus isolating 7.9 g of the title compound as the least polar product during column chromatography.

IR (Film): 3460 (broad), 1773, 1715, 1600, 1590, 1275, 1180, 715 cm$^{-1}$.

11(c)

(1S,5R,6R,7R)-6-[(E)-(3S,4RS)-3-Hydroxy-4-methylnon-1-en-6-inyl]-7-hydroxy-2-oxabicyclo[3,3,0]octan-3-one In analogy to Example 1(i), the 7.9 g of product obtained in the preceding reaction stage were reesterified, thus obtaining 5.6 g of the title compound as a colorless oil.

IR (Film): 3460 (broad), 1765, 1175, 1025, 970 cm$^{-1}$.

11(d)

(1S,5R,6R,7R)-6-[(E)-(3S,4RS)-3-(Tetrahydropyran-2-yloxy)-4-methylnon-1-en-6-inyl]-7-(tetrahydropyran-2-yloxy)-2-oxabicyclo[3,3,0]octan-3-one Analogously to the directions in Example 1(j), the 5.6 g of product obtained in Example 11(c) was reacted to 8.1 g of di-THP ether.

IR (Film): 1770, 1180, 1125, 1075, 1025, 975, 810 cm$^{-1}$.

11(e)

(2RS,3aR,4R,5R,6aS)-4-[(E)-(3S,4RS)-3-(Tetrahydropyran-2-yloxy)-4-methylnon-1-en-6-inyl]-5-(tetrahydropyran-2-yloxy)-perhydrocyclopenta[b]furan-2-ol Analogously to Example 1(h), 8.1 g of lactone [Example 11(d)] was reacted with diisobutyl aluminum hydride to 8.2 g of lactol which was used without further purification in the subsequent stage.

11(f)

(5Z,13E)-(8R,9S,11R,12R,15S,16RS)-9-Hydroxy-11,15-bis(tetrahydropyran-2-yloxy)-16,20-dimethyl-5,13-prostadien-18-ynoic Acid The 8.2 g of lactol obtained according to Example 11(e) was reacted analogously to the directions in Example 1(l) in a Wittig reaction to 6.1 g of acid.

IR (Film): 3480 (broad), 2720, 2660, 1735, 1710, 1130, 1078, 1020, 975, 810 cm$^{-1}$.

11(g)
(5Z,13E)-(8R,9S,11R,12R,15S,16RS)-9-Hydroxy-11,15-bis(tetrahydropyran-2-yloxy)-16,20-dimethyl-5,13-prostadien-18-ynoic Acid Methyl Ester Analogously to the directions in Example 1(m), 6.1 g of carboxylic acid [Example 11(f)] was reacted with diazomethane to 5.8 g of ester.

IR (Film): 3400 (broad), 1735, 1130, 1080, 1020, 975, 810 cm$^{-1}$.

11(h)
(5Z,13E)-(8R,9S,11R,12R,15S,16RS)-16,20-Dimethyl-11,15-bis(tetrahydropyran-2-yloxy)-9-tosyloxy-5,13-prostadien-18-ynoic Acid Methyl Ester Analogously to the reaction as described in Example 1(n), 4 g of the ester obtained according to Example 11(g) was converted into 4.1 g of oily 9α-tosylate.

IR (Film): 2960, 2865, 1735, 1600, 1365, 1175, 975 cm$^{-1}$.

11(i)
(5Z,13E)-(8R,9R,11R,12R,15S,16RS)-9-Hydroxy-11,15-bis(tetrahydropyran-2-yloxy)-16,20-dimethyl-5,13-prostadien-18-ynoic Acid Methyl Ester 4 g of the tosylate produced according to Example 11(h) was reacted analogously to Example 1(o) with potassium nitrite, thus obtaining 1.7 g of the 9β-alcohol as a colorless oil.

IR (Film): 3450, 2950, 1735, 978 cm$^{-1}$.

11(j)
(5Z,13E)-(8R,9R,11R,12R,15S,16RS)-16,20-Dimethyl-11,15-bis(tetrahydropyran-2-yloxy)-9-(p-toluenesulfonyloxy)-5,13-prostadien-18-ynoic Acid Methyl Ester Analogously to Example B 1(p), 1.7 g of the 9β-alcohol produced according to Example 11(i) yielded 1.8 g of the 9β-tosylate in the form of an oil.

IR (Film): 2950, 2860, 1735, 1600, 1495, 1370, 1175, 1030, 1020, 970 cm$^{-1}$.

11(k)
(5Z,13E)-(8R,9R,11R,12R,15S,16RS)-11,15-Dihydroxy-16,20-dimethyl-9-(p-toluenesulfonyloxy)-5,13-prostadien-18-ynoic Acid Methyl Ester The 1.8 g obtained in the preceding reaction stage was reacted to 1.1 g of diol analogously to the directions given in Example 1(q).

IR (Film): 3450, 2960, 2920, 2870, 1735, 1595, 1495, 1360, 1178, 975 cm$^{-1}$.

11(l)
(5Z,13E)-(8R,9S,11R,12R,15S,16RS)-9-Azido-11,15-dihydroxy-16,20-dimethyl-5,13-prostadien-18-ynoic Acid Methyl Ester 1.1 g of the tosylate prepared according to Example 11(k) was reacted analogously to the directions of Example 1(r) with sodium azide, thus obtaining 650 mg of the title compound as a colorless oil.

IR (Film): 3400, 2960, 2930, 2865, 2110, 1753, 975 cm$^{-1}$.

11(m)
(5Z,13E)-(8R,9S,11R,12R,15S,16RS)-9-Azido-11,15-dihydroxy-16,20-dimethyl-5,13-prostadien-18-ynoic Acid The 650 mg obtained in the preceding reaction stage was saponified analogously to Example 1(s), thus obtaining 450 mg of the carboxylic acid as an oil.

IR (Film): 3400 (broad), 2950, 2930, 2875, 2110, 1710, 975 cm$^{-1}$.

EXAMPLE 12

(13E)-(11R,15S,16RS)-11,15-Dihydroxy-16,20-dimethyl-9α,6-nitrilo-13-prosten-19-ynoic Acid A solution of 240 mg of (5Z,13E)-(9S,11R,15S,16RS)-9-azido-11,15-dihydroxy-16,20-dimethyl-5,13-prostadien-19-ynoic acid in 20 ml of ethyl acetate was heated under argon for 24 hours to 70°-75° C. After evaporation of the solvent under vacuum, the residue was purified on silica gel with methylene chloride/10–30% isopropanol as the mobile phase, thus obtaining 160 mg of the title compound as a colorless oil.

IR (Film): 3600, 3400 (broad), 2960, 2860, 1715, 1640, 1020, 975 cm$^{-1}$.

The starting material for the above title compound was produced as follows:

12(a) (1S,5R,6R,7R)-7-Benzoyloxy-6-[(E)-(4RS) 4-methyl-3-oxonon-1-en-7-inyl]-2-oxabicyclo[3,3,0]octan-3-one Analogously to Example 1(g), 7.4 g of the title compound was synthesized from 5.4 g of 3-methyl-2-oxooct-6-inylphosphonic acid dimethyl ester and 6 g of (1S,5R,6R,7R)-6-formyl-7-benzoyloxy-2-oxabicyclo[3,3,0]-octan-3-one [E. J. Corey et al., J. Amer. Chem. Soc. 91: 5675 (1969)].

IR (Film): 1775, 1720, 1686, 1670, 1620, 1600, 1580, 1270, 1182, 715 cm$^{-1}$.

12(b)
(1S,5R,6R,7R)-7-Benzoyloxy-6-[(E)-(3S-4RS)-3-hydroxy-4-methylnon-1-en-7-inyl]-2-oxabicyclo[3,3,0]octan-3-one Analogously to the directions in Example 1(h), the 7.4 g of ketone obtained in the preceding reaction stage was reacted with sodium borohydride, thus isolating 4 g of the title compound as the least polar product after column chromatography.

IR (Film): 3480 (broad), 1775, 1715, 1603, 1590, 1275, 1180, 715 cm$^{-1}$.

12(c)
(1S,5R,6R,7R)-6-[(E)-(3S,4RS)-3-Hydroxy-4-methylnon-1-en-7-inyl]-7-hydroxy-2-oxabicyclo[3,3,0]octan-3-one In analogy to Example 1(i), the 4 g obtained in the preceding reaction stage was reesterified, thus obtaining 2.6 g of the title compound as a colorless oil.

IR (Film): 3460 (broad), 1765, 1175, 1030, 970 cm$^{-1}$.

12(d)
(1S,5R,6R,7R)-6-[(E)-(3S,4RS)-3-(Tetrahydropyran-2-yloxy)-4-methylnon-1-en-7-inyl]-7-(tetrahydropyran-2-yloxy)-2-oxabicyclo[3,3,0]octan-3-one Analogously to the directions given in Example 1(j), the 2.6 g obtained in Example 12(c) was reacted to 3.8 g of di-THP ether.

IR (Film): 1770, 1180, 1130, 1075, 1020, 975, 810 cm$^{-1}$.

12(e)

(2RS,3aR,4R,5R,6aS)-4-[(E)-(3S,4RS)-3-(Tetrahydropyran-2-yloxy)-4-methylnon-1-en-7-inyl]-5-(tetrahydropyran-2-yloxy)perhydrocyclopenta[b]furan-2-ol In analogy to Example 1(h), 3.8 g of lactone [Example 12(d)] was reacted with diisobutyl aluminum hydride to obtain 4 g of lactol which was used without further purification in the subsequent stage.

12(f)

(5Z,13E)-(8R,9S,11R,12R,15S,16RS)-9-Hydroxy-11,15-bis(tetrahydropyran-2-yloxy)-16,20-dimethyl-5,13-prostadien-19-ynoic Acid The 4 g of lactol obtained according to Example 12(e) was reacted analogously to the directions given in Example 1(l) in a Wittig reaction to 2.9 g of acid.

IR (Film): 3480 (broad), 2730, 2660, 1735, 1710, 1130, 1080, 1020, 975, 810 cm$^{-1}$.

12(g)

(5Z,13E)-(8R,9S,11R,12R,15S,16RS)-9-Hydroxy-11,15-bis(tetrahydropyran-2-yloxy)-16,20-dimethyl-5,13-prostadien-19-ynoic Acid Methyl Ester Analogously to the directions in Example 1(m), 2.9 g of carboxylic acid [Example 1(f)] was reacted with diazomethane to 2.8 g of ester.

IR (Film): 3400 (broad), 1738, 1132, 1078, 1020, 975, 810 cm$^{-1}$.

12(h)

(5Z,13E)-(8R,9S,11R,12R,15S,16RS)-16,20-Dimethyl-11,15-bis(tetrahydropyran-2-yloxy)-9-tosyloxy-5,13-prostadien-19-ynoic Acid Methyl Ester 2.8 g of the ester obtained according to Example 12(g) was converted analogously to the reaction described in Example 1(n) into 2.7 g of oily 9α-tosylate.

IR (Film): 2960, 2870, 1735, 1602, 1360, 1175, 975 cm$^{-1}$.

12(i)

(5Z,13E)-(8R,9R,11R,12R,15S,16RS)-9-Hydroxy-11,15-bis(tetrahydropyran-2-yloxy)-16,20-dimethyl-5,13-prostadien-19-ynoic Acid Methyl Ester 2.7 g of the tosylate produced according to Example 12(h) was reacted with potassium nitrite in analogy to Example 1(o), thus obtaining 1 g of the 9β-alcohol as a colorless oil.

IR (Film): 3450, 2950, 1735, 980 cm$^{-1}$.

12(j)

(5Z,13E)-(8R,9R,11R,12R,15S,16RS)-16,20-Dimethyl-11,15-bis(tetrahydropyran-2-yloxy)-9-(p-toluenesulfonyloxy)-5,13-prostadien-19-ynoic Acid Methyl Ester Analogously to Example 1(p), 1 g of the 9β-alcohol prepared according to Example 12(i) yielded 1.1 g of the 9β-tosylate as an oil.

IR (Film): 2960, 2860, 1735, 1600, 1495, 1365, 1175, 1030, 1020, 975 cm$^{-1}$.

12(k)

(5Z,13E)-(8R,9R,11R,12R,15S,16RS)-11,15-Dihydroxy-16,20-dimethyl-9-(p-toluenesulfonyloxy)-5,13-prostadien-19-ynoic Acid Methyl Ester The 1.1 g of product obtained in the preceding reaction stage was reacted to 0.67 g of diol analogously to the directions given in Example 1(q).

IR (Film): 3450, 2955, 2920, 2870, 1735, 1595, 1495, 1360, 1175, 978 cm$^{-1}$.

12(l)

(5Z,13E)-(8R,9S,11R,12R,15S,16RS)-9-Azido-11,15-dihyroxy-16,20-dimethyl-5,13-prostadien-19-ynoic Acid Methyl Ester 650 mg of the tosylate produced according to Example 12(k) was reacted analogously to the directions of Example 1(r) with sodium azide, thus obtaining 360 mg of the title compound as a colorless oil.

IR (Film): 3400, 2960, 2930, 2870, 2110, 1735, 980 cm$^{-1}$.

12(m)

(5Z,13E)-(8R,9S,11R,12R,15S,16RS)-9-Azido-11,15-dihydroxy-16,20-dimethyl-5,13-prostadien-19-ynoic Acid The 360 mg obtained in the preceding reaction stage was saponified analogously to Example 1(s), thus producing 240 mg of the carboxylic acid as an oil.

IR (Film): 3400 (broad), 2955, 2930, 2875, 2110, 1712, 978 cm$^{-1}$.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. An azaprostacyclin of the formula

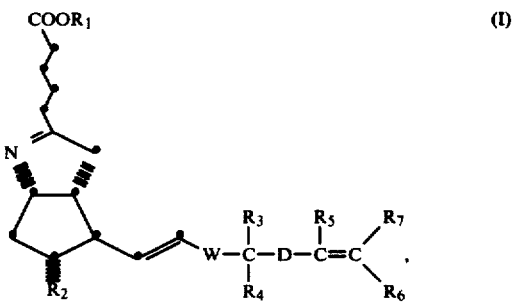

wherein

R$_1$ is (a) hydrogen, (b) C$_{1-10}$ alkyl, (c) C$_{1-10}$ alkyl substituted by halogen; C$_{1-4}$ alkoxy; C$_{6-10}$ aryl; C$_{6-10}$ aryl substituted by 1-3 halogen atoms, a phenyl group, 1-3 C$_{1-4}$ alkyl groups or a chloromethyl, fluoromethyl, trifluoromethyl, carboxy, hydroxy or C$_{1-4}$ alkoxy group; di-C$_{1-4}$-alkylamino; or tri-C$_{1-4}$-alkylammonium; (d) C$_{4-10}$ cycloalkyl, (e) C$_{4-10}$ cycloalkyl substituted by C$_{1-4}$ alkyl, (f) C$_{6-10}$ aryl, (g) C$_{6-10}$ aryl substituted by 1-3 halogen atoms, a phenyl group, 1-3 C$_{1-4}$ alkyl groups or a chloromethyl, fluoromethyl, trifluoromethyl, carboxy, hydroxy or $C_{1-4}$ alkoxy group, (h) an aromatic heterocycle of 5 or 6 ring atoms one of which is O, N or S, the remainder being carbon atoms, (i) phenacyl, or (j) phenacyl substituted on the phenyl ring by bromine, phenyl, $C_{1-4}$-alkoxy, or di-$C_{1-4}$-alkoxy,

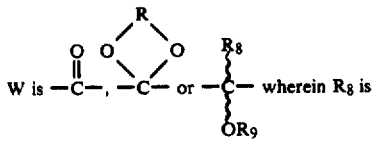

hydrogen or alkyl of 1-5 carbon atoms, $R_9$ is hydrogen, tetrahydropyranyl, tetrahydrofuranyl, α-ethoxyethyl, trimethylsilyl, dimethyl-tert-butylsilyl, tribenzylsilyl or an acyl group of a $C_{1-15}$-hydrocarbon carboxylic or sulfonic acid, the $OR_9$-group can be in the α- or β-position, and R is $-(CH_2)_{2-5}-$,

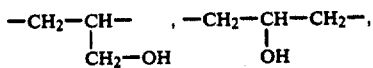

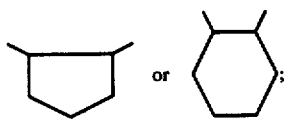

$R_2$ is OH or $OR_9$, $R_3$ and $R_4$ each independently is hydrogen, alkyl of 1-5 carbon atoms, or fluorine, D is $-(CH_2)_{1\ or\ 2}-$, $-(CH_2)_{1\ or\ 2}-$ substituted by $C_{1-5}$-alkyl or together with $R_6$ forms a ring of the formula

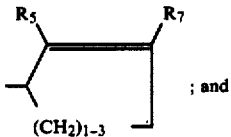

(1) when D is optionally substituted alkylene as defined above, $R_5$ is H or $C_{1-2}$-alkyl and $R_6$ and $R_7$ each independently is H or $C_{1-2}$-alkyl or one is $C_{1-2}$alkyl and the other is halo; and (2) when D forms a ring with $R_6$, $R_5$ and $R_7$ each independently is H or $C_{1-2}$alkyl;

or for the compounds wherein $R_1$ is H, a physiologically compatible salt thereof.

2. A compound of claim 1 wherein $R_2$ is OH and $R_1$ is H.

3. A compound of claim 1 wherein D is $-CH_2-$.

4. A compound of claim 1 wherein at least one of $R_6$ and $R_7$ is $-CH_3$.

5. (13E)-(11R,15S,16RS)-11,15-Dihydroxy-16,19-dimethyl-9α,6-nitrilo-13,18-prostadienoic acid a compound of claim 1.

6. (13E)-(11R,15R,16RS)-11,15-Dihydroxy-16,19-dimethyl-9α,6-nitrilo-13,18-prostadienoic acid a compound of claim 1.

7. (13E)-(11R,15S)-11,15-Dihydroxy-19-methyl-9α,6-nitrilo-13,18-prostadienoic acid a compound of claim 1.

8. (13E,18Z)-(11R,15S,16RS)-11,15-Dihydroxy-19-chloro-16-methyl-9α,6-nitrilo-13,18-prostadienoic acid a compound of claim 1.

9. (13E)-(11R,15S)-11,15-Dihydroxy-16-(2-cyclohexenyl)-17,18,19,20-tetranor-9α,6-nitrilo-13-prostenoic acid a compound of claim 1.

10. (13E)-(11R,15S,16RS)-11,15-Dihydroxy-16-methyl-16-(2-cyclopenten-1-yl)-17,18,19,20-tetranor-9α,6-nitrilo-13-prostenoic acid a compound of claim 1.

11. (13E)-(11R,15S,16RS)-11,15-Dihydroxy-16,19-dimethyl-9α,6-nitrilo-13,18-prostadienoic acid methyl ester a compound of claim 1.

12. Tris(hydroxymethyl)aminomethane salt of (13E)-(11R,15S,16RS)-11,15-Dihydroxy-16,19-dimethyl-9α,6-nitrilo-13,18-prostadienoic acid a compound of claim 1.

13. (13E)-(11R,15S,16RS)-11,15-Dihydroxy-16,19-dimethyl-9α,6-nitrilo-13,18-prostadienoic acid butyl ester a compound of claim 1.

14. A pharmaceutical composition useful for lowering blood pressure comprising an effective amount of a compound of claim 1 and a pharmaceutically acceptable carrier.

15. A method of lowering blood pressure in a patient in need of such treatment comprising administering an effective amount of a compound of claim 1 to the patient.

16. A compound of claim 1 wherein D together with $R_6$ forms a ring.

17. A compound of claim 1 wherein one of $R_6$ or $R_7$ is halo.

18. A compound of claim 17 wherein one of $R_6$ or $R_7$ is chloro.

19. A compound of claim 1 wherein $R_6/R_8$ is a bond and $R_7$ is H or ethyl.

20. A compound of claim 1 wherein $R_6$ is H, $C_{1-2}$-alkyl or halo.

* * * * *